United States Patent
Beck

(10) Patent No.: US 8,917,290 B2
(45) Date of Patent: Dec. 23, 2014

(54) DIGITAL IMAGE TEMPLATING

(75) Inventor: Paul Richard Beck, Chicago, IL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 162 days.

(21) Appl. No.: 13/018,021

(22) Filed: Jan. 31, 2011

(65) Prior Publication Data

US 2012/0194505 A1  Aug. 2, 2012

(51) Int. Cl.
*G09G 5/00* (2006.01)
*G09G 5/36* (2006.01)
*G06T 11/00* (2006.01)
*G06F 19/00* (2011.01)

(52) U.S. Cl.
CPC ............ *G09G 5/363* (2013.01); *G09G 2370/02* (2013.01); *G06T 11/00* (2013.01); *G09G 2340/0407* (2013.01); *G06F 19/321* (2013.01); *G09G 2380/08* (2013.01)
USPC ......................................................... 345/660

(58) Field of Classification Search
CPC ................................ G06T 19/10; G06T 12/20
USPC ......................................................... 345/660
See application file for complete search history.

(56) References Cited

U.S. PATENT DOCUMENTS

| | | | |
|---|---|---|---|
| 5,360,446 A | 11/1994 | Kennedy | |
| 5,400,513 A | 3/1995 | Duffield | |
| 5,682,886 A | 11/1997 | Delp et al. | |
| 5,769,092 A | 6/1998 | Williamson, Jr. | |
| 5,799,055 A | 8/1998 | Peshkin et al. | |
| 5,832,422 A | 11/1998 | Wiedenhoefer | |
| 6,205,411 B1 | 3/2001 | DiGioia et al. | |
| 6,272,247 B1 * | 8/2001 | Manickam et al. | ........... 382/217 |
| 6,334,157 B1 | 12/2001 | Oppermann et al. | |
| 6,342,905 B1 | 1/2002 | Diedrich et al. | |
| 6,424,332 B1 | 7/2002 | Powell | |
| 6,459,948 B1 | 10/2002 | Ateshian et al. | |

(Continued)

FOREIGN PATENT DOCUMENTS

EP    2405336 A1    11/2012

OTHER PUBLICATIONS

Siti Fairuz Yusof, Riza Sulaiman, Lee Thian Seng, Abdul Yazid Mohd. Kassim, Suhail Abdullah, Shahril Yusof, Masbah Omar, and Hamzaini Abdul Hamid, "Development of Total Knee Replacement Digital Templating Software"IVIC 2009, LNCS 5857, pp. 180-190, 2009.*

(Continued)

*Primary Examiner* — Javid A. Amini
*Assistant Examiner* — Jin Ge
(74) *Attorney, Agent, or Firm* — Harness, Dickey

(57) ABSTRACT

Methods and devices for digital image templating are presented. According to example embodiments, a computing device may match a template image (e.g., an implant) to a target image (e.g., a bone structure). The both the target image and the template image may be displayed on an output of the computing device. The displayed template image may be oriented with respect to the displayed target image according to at least a scale (e.g., a magnification level of the template image). Based on received input, at least the scale of the displayed template image may be adjusted so that the adjusted displayed template image substantially fits the part of the displayed target image. Then, based on this fit, a physical template size may be selected from a discrete range of physical template sizes.

23 Claims, 17 Drawing Sheets

(56) References Cited

U.S. PATENT DOCUMENTS

| | | | |
|---|---|---|---|
| 6,573,915 | B1 | 6/2003 | Sivan et al. |
| 6,701,174 | B1 | 3/2004 | Krause et al. |
| 6,772,026 | B2 | 8/2004 | Bradbury et al. |
| 6,932,842 | B1 | 8/2005 | Litschko et al. |
| 7,158,692 | B2* | 1/2007 | Chalana et al. ............... 382/294 |
| 7,383,073 | B1 | 6/2008 | Abovitz et al. |
| 7,388,972 | B2* | 6/2008 | Kitson .......................... 382/128 |
| 7,468,075 | B2 | 12/2008 | Lang et al. |
| 7,534,263 | B2 | 5/2009 | Burdulis, Jr. et al. |
| 7,981,158 | B2 | 7/2011 | Fitz et al. |
| 7,983,777 | B2 | 7/2011 | Melton et al. |
| 8,066,708 | B2 | 11/2011 | Lang et al. |
| 8,077,950 | B2 | 12/2011 | Tsougarakis et al. |
| 2004/0151399 | A1* | 8/2004 | Skurdal et al. ................ 382/266 |
| 2005/0038338 | A1 | 2/2005 | Bono et al. |
| 2005/0059873 | A1* | 3/2005 | Glozman et al. .............. 600/407 |
| 2005/0162419 | A1* | 7/2005 | Kim et al. ..................... 345/419 |
| 2006/0242159 | A1 | 10/2006 | Bishop et al. |
| 2006/0287733 | A1 | 12/2006 | Bonutti |
| 2007/0118055 | A1 | 5/2007 | McCombs |
| 2007/0118243 | A1 | 5/2007 | Schroeder et al. |
| 2007/0198022 | A1 | 8/2007 | Lang et al. |
| 2007/0226986 | A1 | 10/2007 | Park et al. |
| 2007/0272747 | A1 | 11/2007 | Woods et al. |
| 2008/0063302 | A1* | 3/2008 | Russak et al. ................. 382/296 |
| 2008/0063304 | A1 | 3/2008 | Russak et al. |
| 2008/0148167 | A1* | 6/2008 | Russak et al. ................. 715/769 |
| 2008/0180406 | A1* | 7/2008 | Han et al. ...................... 345/173 |
| 2008/0189358 | A1* | 8/2008 | Charles ......................... 709/203 |
| 2008/0319448 | A1 | 12/2008 | Lavallee et al. |
| 2009/0043556 | A1 | 2/2009 | Axelson et al. |
| 2009/0089081 | A1* | 4/2009 | Haddad .............................. 705/2 |
| 2009/0222014 | A1 | 9/2009 | Bojarski et al. |
| 2009/0259967 | A1* | 10/2009 | Davidson et al. ............. 715/799 |
| 2009/0306676 | A1 | 12/2009 | Lang et al. |
| 2009/0312805 | A1 | 12/2009 | Lang et al. |
| 2010/0030231 | A1 | 2/2010 | Revie et al. |
| 2010/0080491 | A1* | 4/2010 | Ohnishi ........................ 382/298 |
| 2010/0134425 | A1* | 6/2010 | Storrusten .................... 345/173 |
| 2010/0217270 | A1 | 8/2010 | Polinski et al. |
| 2010/0274534 | A1 | 10/2010 | Steines et al. |
| 2010/0281678 | A1 | 11/2010 | Burdulis, Jr. et al. |
| 2010/0295803 | A1* | 11/2010 | Kim et al. ..................... 345/173 |
| 2010/0303313 | A1 | 12/2010 | Lang et al. |
| 2010/0303317 | A1 | 12/2010 | Tsougarakis et al. |
| 2010/0303324 | A1 | 12/2010 | Lang et al. |
| 2010/0305907 | A1 | 12/2010 | Fitz et al. |
| 2010/0329530 | A1 | 12/2010 | Lang et al. |
| 2011/0029091 | A1 | 2/2011 | Bojarski et al. |
| 2012/0008848 | A1 | 1/2012 | Beck |

OTHER PUBLICATIONS

Monika Michalíková, Lucia Bednarčíková, Martin Petrík, Jozef Živčák, Richard Raši, "The Digital Pre-Operative Planning of Total Hip Arthroplasty", Acta Polytechnica Hungarica, vol. 7, No. 3, 2010.*

S. Azrulhizam, S. Riza, K.H., Mohammad and M.K., Abdul Yazid and S. Abdullah, "Scaling Technique for Digital Implant in Medical Images Using Pixel Density Algorithm", European Journal of Scientific Research, 47 (1), 24-32. 2010.*

Y. Kosashvili, N. Shasha, E. Olschewski, O. Safir, L. White, A. Gross and D. Backstein, "Digital versus conventional templating techniques in preoperative planning for total hip arthroplasty", Can J Surgery, 52(1): 6-11, 2009.*

Genesis Digital Imaging, "Orthopedic Digital Pre-Operative Planning & Templating Solution", 2009.*

H. Handels, J. Ehrhardt, W. Plötz, S.J. Pöppl, "Three-dimensional Planning and Simulation of Hip Operations and Computer-Assisted Construction of Endoprostheses in Bone Tumor Surgery", Jun. 1999.*

William J Murzic, Zeev Glozman, and Paula Lowe, "Digital Templating in Total Hip Replacement", US Musculo Skeletal Review 2006.*

Ely Liviu Steinberg, Nadav Shasha, Aharon Menahem and Shmuel Dekel, "Preoperative planning of total hip replacement using the TraumaCad™ system", Archives of Orthopaedic and Trauma Surgery vol. 130, No. 12 (2010), 1429-1432, DOI: 10.1007/s00402-010-1046-y.*

Moscovich, T. and Hughes, J.F. (2006) Multi-finger cursor techniques. Proc. GI '06. Toronto: CIPS, 1-7.*

EP Application No. 11 17 2626, European Search Report mailed Nov. 10, 2011.

Yusof et al., "Development of Total Knee Replacement Digital Templating Software," Visual Informatics: Bridging Research and Practice, Springer Berlin Heidelberg, Berlin, Heidelberg, pp. 180-190 (Nov. 11, 2009).

Anonymous, "Iconico Screen Calipers," Jan. 2, 2010, 16 pages, Retrieved from the Internet: URL: http://web.archiv.org/web/20100102043404/http://iconico.com/caliper/index.aspx [retrieved on Oct. 20, 2011].

Steinberg et al., "Preoperative planning of total hip replacement using the TraumaCad™ system," Archives of Orthopaedic and Trauma Surgery: Including Arthroscopy and Sports Medicine, vol. 130, No. 12, pp. 1429-1432 (Jan. 13, 2010).

Benjamin Wulfe, "Using .NET: Deliver the Power of Spy++ to Windows Forms with Our New Tool," from the World Wide Web, mdsn.microsoft.com/.../cc163617.aspx, printed Mar. 19, 2010.

Richard King et al., "A novel method of accurately calculating the radiographic magnification of the hip," Warwick Orthopaedics, 2009.

OrthoView, "Joint Replacement," from the World Wide Web, c:/.../Joint Replacement - OrthoView.h..., printed on Mar. 19, 2010.

Wikipedia, "Photogrammetry," from the World Wide Web, en.wikipedia.org/wiki/Photogrammetry, printed on Jul. 17, 2010.

Project SIKULI, http://groups,csail.mit.edu/uid/sikuli/, printed from the World Wide Web on Jul. 8, 2010.

TraumaCad Touch New! and Trauma Cad OrthoWeb, Voyant Health, 2 pages, MK200197_B (Dec. 2009).

TraumaCad Touch Guide, BrainLAB's Digital Lightbox, Orthocrat, www.orthocrat.com, 12 pages.

"TraumaCad User's Guide Version 2.2," Voyant Health, A Voyant Health Ltd. Document, 206 pages (2010).

Brannigan et al., A Framework for "Need to Know" Authorizations in Medical Computer Systems: Responding to the Constitutional Requirements, JAMIA, Proceedings of the 18th Annual Symposium on Computer Applications in Medical Care, pp. 396-396 (1994).

Wikipedia, "Distributed Computing", Jan. 5, 2009.

"Screenshot," Wikipedia, the free encyclopedia, May 22, 2009.

About.com, TechSmith Snagit 8 Screen Capture Utility for Windows, Apr. 1, 2008.

Wikipedia, the free encyclopedia, Metadata, May 29, 2009.

Wikipedia, the free encyclopedia, HUD (video gaming), Dec. 6, 2009.

* cited by examiner

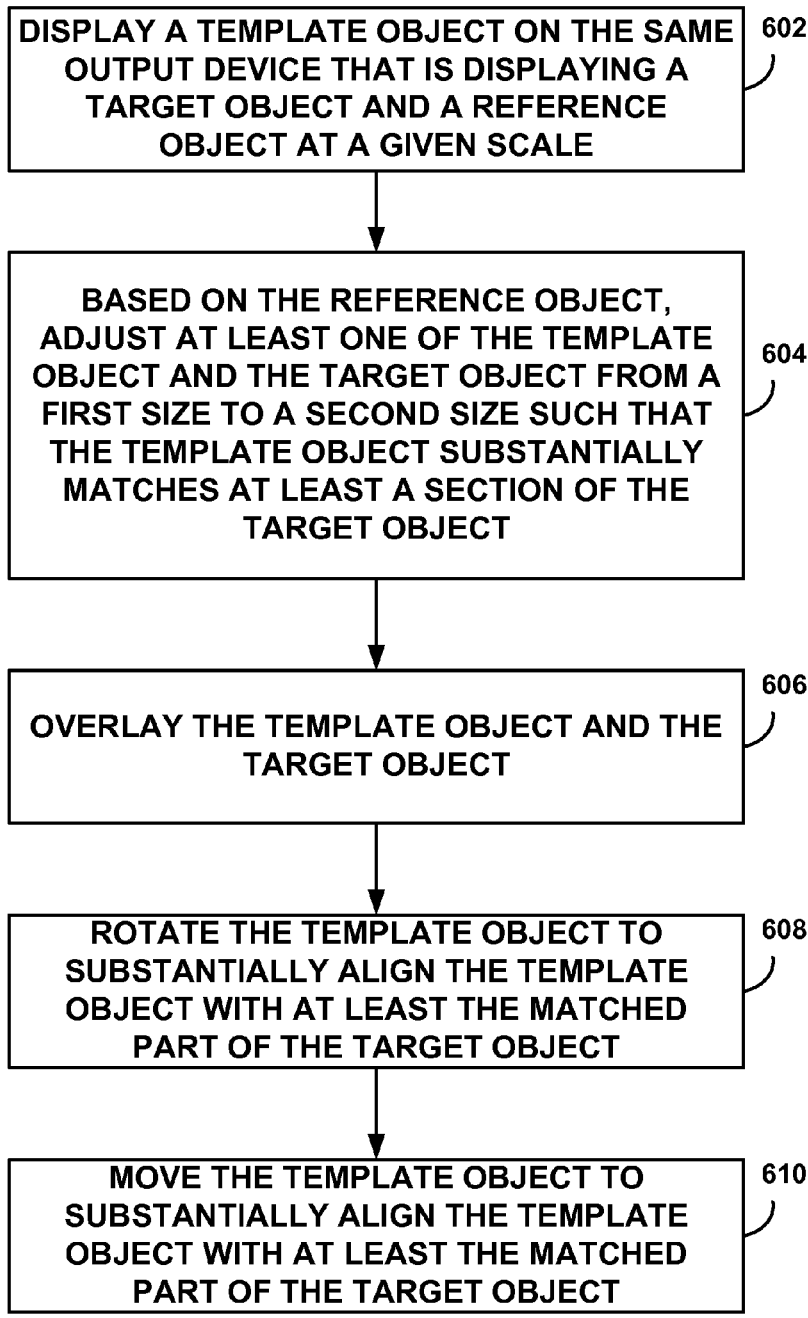

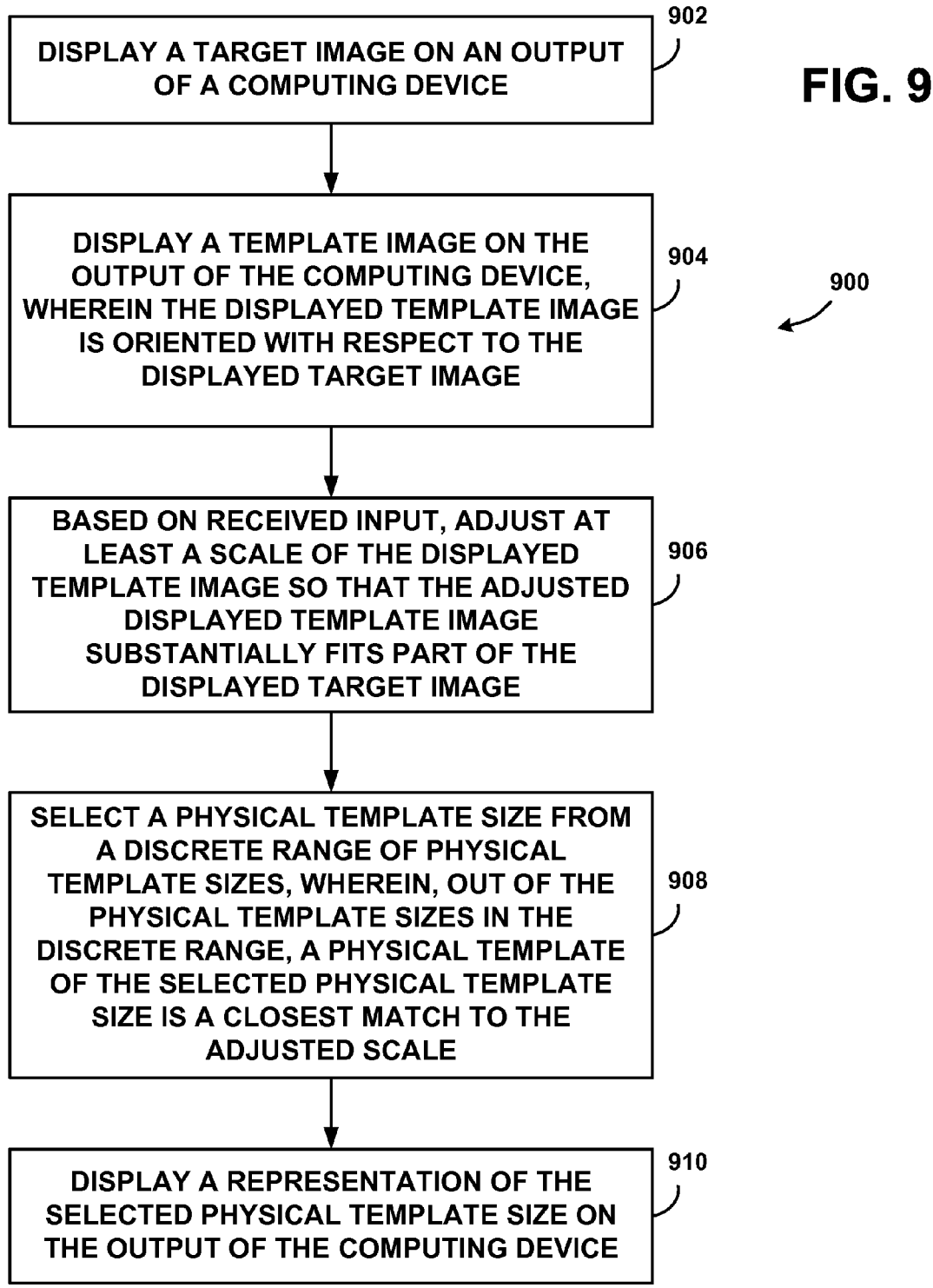

DIGITAL IMAGE TEMPLATING

BACKGROUND

Orthopedic joint replacement and stabilization surgery has grown in popularity over the course of the last several decades. Advances in technology have made procedures such as hip replacement, knee replacement, and bone stabilization commonplace. Joint replacement procedures typically involve replacing a damaged joint with a prosthetic implant that is shaped in a way that allows movement similar to that of a healthy joint. Stabilization procedures typically involve bracing or fixating an injured bone so that it heals properly. Implants used in both types of procedures may be made from metal, plastic, ceramic, or some other substance.

In order for an orthopedic replacement procedure to be successful, a physician must be able to anticipate both the type and size of implant needed. Doing so reduces the risk of complications during the procedure, including nerve injury, instability, intraoperative fracture while inserting the implant, postoperative pain, and even failure to have the correct hardware available. Use of a proper implant also enables the procedure to be performed safely and accurately, providing strong fixation between implant and bone. Thus, being able to anticipate both the type and size of the implant is desirable to ensure the procedure's success.

Traditionally, a physician would manually size implants to radiographic (i.e., x-ray) images of the patient's joint and the associated bone structure. The physician would place a clear sheet, or template, containing an outline in the shape of the implant over the radiograph. This outline may include points, solid lines, dashed lines, or dotted lines, at least some of which may correspond to common bone structure or physiological reference points. Given that radiographic images are typically magnified by approximately 10% to 25%, the template is also typically magnified to account for the anticipated magnification of the patient's bone structure when a radiograph is taken.

The physician could then line up the template to a section of the patient's bone structure. By using multiple templates of different sizes in essentially a trial-and-error procedure, the physician would eventually determine a size for the actual implant hardware. However, this method is often inaccurate due to an inherent weakness. Traditional templates can only provide one magnification. As a result, it is usually an average for the entire population. Yet, magnification in the general population varies widely as it is proportional to body habitus. For example, extremely large patients have much greater magnification on their radiographs than small patients. As a result, this traditional procedure is subject to the risk that an implant of the wrong size will be used.

In order to overcome this problem, some physicians place a sizing marker on the radiograph which enables them to more accurately determine the magnification of the radiograph. Once the radiograph has been templated, the physician then adjusts the final result by the determined magnification. This method ultimately fails because the template is not resized to the correct magnification before being placed over the radiograph. As a result, the incorrectly sized template is placed in the incorrect position. Unfortunately, any template in the incorrect position cannot accurately determine the size of implant hardware needed. Therefore, using a magnification marker for traditional templating does not improve the accuracy of the templating process.

To improve the accuracy of traditional templating, many physicians now use digital templating. With digital templating, the physician views the radiographic image on a computer, and uses a computer representation of the template to attempt to fit the template to the bone to be replaced or stabilized. Digital templating has a significant advantage over traditional methods in that digital templates are not limited to one size magnification. Templating software enables either the templates or the radiograph to be adjusted to the correct magnification prior to placement of the template. Nonetheless, while digital templating addresses some of the problems of orthopedic templating, current systems have several disadvantages, in that they are proprietary, inflexible, prohibitively expensive, difficult to set up and maintain, and hard to use.

OVERVIEW

The embodiments herein are generally directed to reducing the cost of digital image templating while improving its speed and ease of use. In particular, a digital representation of a radiograph may be viewed on a computer screen. The radiograph may depict a reference object of a known size and a bone structure. The magnification level of the radiograph may be unknown. Therefore, in order to determine a properly-sized orthopedic implant, the magnification level of the radiograph should be determined so that the actual physical size of the bone structure can be ascertained.

Preferably independent of the application being used to view the radiograph, a templating application may be executed and displayed on at least part of the computer screen. The templating application may transparently or semi-transparently overlay the radiograph viewing application, thereby allowing a user (e.g., a physician, physician's assistant, technician, nurse, sales representative, etc.) to simultaneously view output from both applications.

The templating application may measure the size of the reference object to determine the magnification level of the radiographic image. For instance, if the reference object is a disc or ball with a 25 millimeter diameter, measuring the size of the disc or ball as it appears on the computer screen can be used to determine the actual size of the bone structure.

Then, from the templating application, the user may select a template of an implant type (e.g., a hip or knee joint) to match the bone structure displayed in the radiograph. Further, the user may select an implant size from one of potentially several discrete ranges of implant sizes. The chosen template may be displayed on the computer screen scaled to match the magnification level of the radiograph. In this way, the user can rotate and move the template on the radiographic image until the template substantially matches the section of the bone structure that the implant is intended to replace or stabilize. If the user finds that the chosen template is not a good match for the bone structure, the user may select a template of a different type or size from the discrete range of implant sizes, and attempt to match this template to the bone structure. The user may continue this process until a properly-sized template is found. Alternatively, the templating application may suggest, recommend, or choose sizes for the user. For some orthopedic procedures, multiple templates may be selected, sized, and matched to the bone structure one at a time or simultaneously.

Accordingly, in a first example embodiment, a computing device may facilitate or undertake substantially matching a template object (e.g., a representation of an implant) to a target object (e.g., a bone structure). Preferably, the template object represents at least a section of the target object. The target object may be displayed in a radiograph, along with a reference object of known size.

From the known size of the reference object, the computing device may determine the magnification level, or scale, at which the target object and reference object are represented.

Then, the computing device may adjust at least one of the template object and the target object so that the template object substantially matches at least the represented section of the target object. If the template object is adjusted, the initial size of the template object may be chosen from a discrete range of sizes, and the final size of the template object may be based on applying the scale to the initial size.

The computing device may also overlay the template object and the target object. To do so, the template object, the target object, or both may be displayed in a transparent or semi-transparent fashion so that both the template object and the target object are visible. The computing device may also rotate or move the template object to substantially align the template object with at least the matched part of the target object. The alignment may occur automatically or with the guidance of a user.

Advantageously, the computer application, or program, that displays the reference object and the target object may be different from the computer application that displays and sizes the template object. These two applications may be independent of one another, not sharing program instructions or memory. Further, these two applications might not communicate with one another. Thus, the application that displays the reference object and the target object may be an image viewing application, and the application that displays and sizes the template object may be a templating application.

This independent arrangement may serve to simplify the hardware or software architecture of the digital templating system. The image viewing application can be any type of application, including but not limited to, a traditional image viewer such as ADOBE PHOTOSHOP®, a specialized medical image viewer, an email client, or a web browser. The templating application may independently execute in the foreground or background on the same computing device. Thus, the templating application can operate with any application that displays the reference object and the target object, and neither this application nor the templating application are burdened by the effort and complexity of integrating the functions of one into the other.

Further, the templating application does not need to be integrated into existing medical imaging software as a module or plug-in, nor does the templating application need to be integrated within the security infrastructure of complex computer networks that span multiple hospitals, physician's offices, and imaging centers.

In a second example embodiment, a computing device may also facilitate or undertake substantially matching a template image (e.g., a representation of an implant) to a target image (e.g., a representation of a bone structure). At least part of the template image may correspond to at least a part of the target image.

The both the target image and the template image may be displayed on an output of the computing device. The displayed template image may be oriented with respect to the displayed target image. Based on received input, at least a scale of the displayed template image may be adjusted so that the adjusted displayed template image substantially fits the part of the displayed target image. The scale may represent, for example, a magnification level of the template image.

A physical template size may be selected from a discrete range of physical template sizes. This selection may be made so that, out of the physical template sizes in the discrete range, a physical template of the selected physical template size is a closest match to the adjusted scale. Then, a representation of the selected physical template size may be displayed on the output of the computing device.

In some possible variations of the second example embodiment, the displayed template image may be oriented with respect to the displayed target image according to a rotation and a position. Therefore, the rotation and position of the displayed template image may also be adjusted so that the adjusted displayed template image substantially fits the part of the displayed target object. At least two of the scale, the rotation, and the position of the displayed template image may be adjusted substantially simultaneously, for instance, via a multitouch-enabled touchscreen interface.

In a third example embodiment, a computing device may likewise facilitate or undertake substantially matching a template image to a target image. Again, at least part of the template image may represent at least a part of the target image, and both the target image and the template image may be displayed on an output of the computing device. The displayed template image may be oriented with respect to the displayed target image.

However, in this embodiment, a scale of the displayed template image may correspond to a first physical template size of a discrete range of physical template size. Then, based on received input, at least the scale of the displayed template image may be adjusted to a second physical template size of the discrete range of template sizes. Preferably, the adjusted displayed template image substantially fits the part of the target object.

Not unlike the second example embodiment, in some possible variations of the third example embodiment the displayed template image may also be oriented with respect to the displayed target image according to a rotation and a position. Accordingly, the rotation and position of the displayed template image may also be adjusted so that the adjusted displayed template image substantially fits the part of the displayed target object. At least two of the scale, the rotation, and the position of the displayed template image may be adjusted substantially simultaneously, for instance, via a multitouch-enabled touchscreen interface.

Despite the focus of the example embodiments herein, these embodiments also are not limited to orthopedics. In addition to the uses described above, the present invention can be used in fields such as architecture, space planning, and civil engineering, or any other field where a template is matched to features depicted in an image. Moreover, the methods and devices disclosed herein may operate on or make use of a wide range of physical or logical computer hardware components, and may be implemented on any type of software platform.

These and other aspects and advantages will become apparent to those of ordinary skill in the art by reading the following detailed description, with reference where appropriate to the accompanying drawings. Further, it should be understood that the foregoing overview is merely for purposes of example and is not intended to limit the scope of the invention as claimed.

BRIEF DESCRIPTION OF THE DRAWINGS

FIG. 6 is a first flow chart, in accordance with an example embodiment;

FIG. 9 is a third flow chart, in accordance with an example embodiment; and

DESCRIPTION

I. Network Architecture and Devices

Disclosed herein are methods and devices for digital image templating. On a computer screen, a template object representing an orthopedic implant may be overlaid on or with a digital representation of a radiograph. The radiograph may depict a bone structure. The template object or the representation of the radiograph may then be scaled, rotated, moved, twisted, bent, or otherwise manipulated until the template object substantially matches the size and alignment of at least a section of the bone structure.

Figure 1:
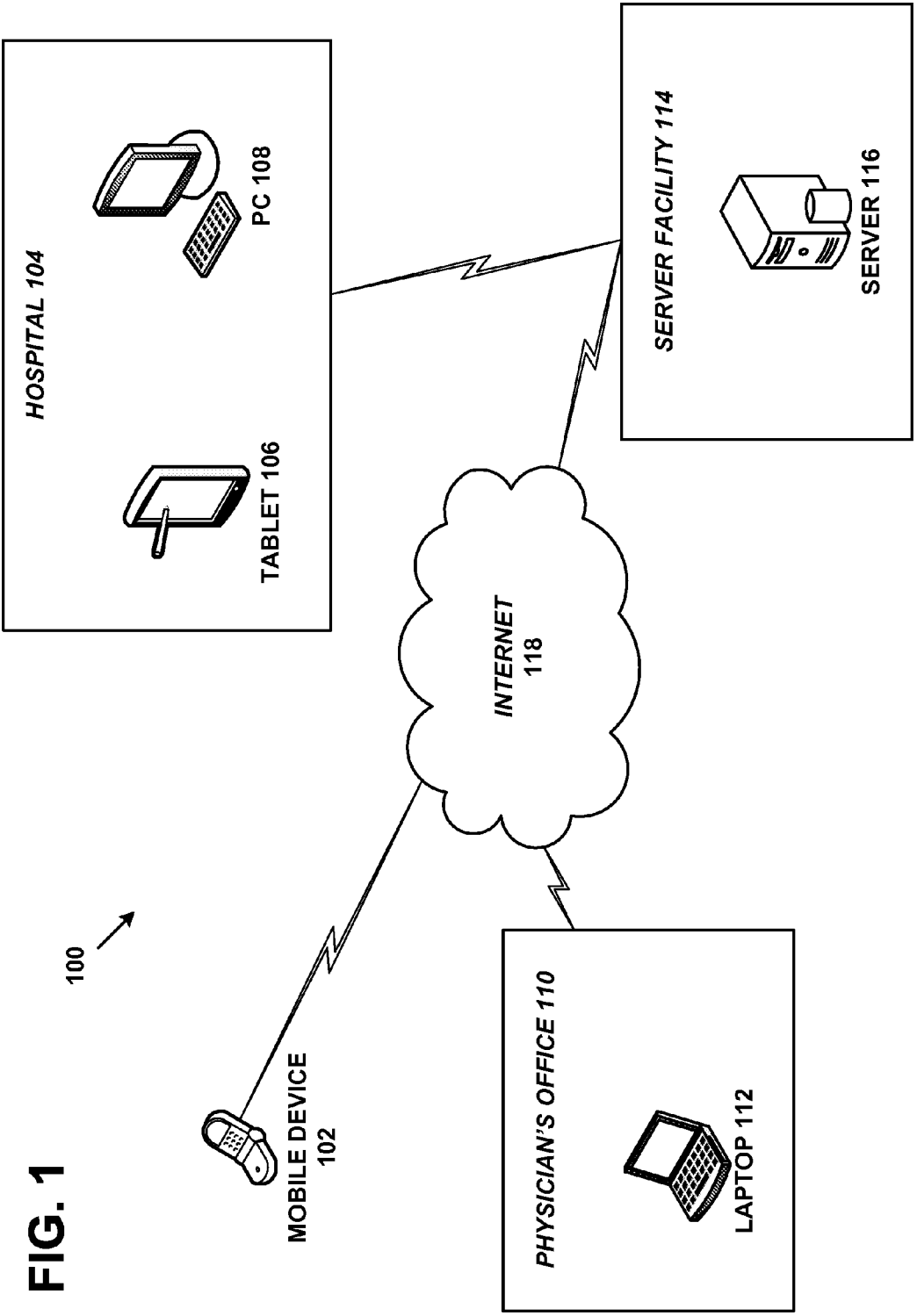
FIG. 1 depicts a number of computing devices, arranged in several physical locations, in accordance with an example embodiment.

FIG. 1 depicts a computing system 100. At a high level, the computing system 100 comprises multiple client devices in multiple physical locations accessing data at a server facility 114. As one example, a mobile device 102, such as a cell phone, communicates wirelessly with the Internet 118 and, in turn, with the server facility 114. In another example, a tablet device 106 and a personal computer (PC) 108 at a hospital 104 communicate using wireless or wireline technologies via the Internet 118 and, in turn, with the server facility 114. In yet another example, a laptop 112 at a physician's office 110 also communicates using wireless or wireline technologies via the Internet 118 and, in turn, with the server facility 114.

Preferably, the server facility 114 contains at least a server device 116 with access to an image database. The images in the database may include depictions of radiographs, indexed by patient, by medical procedure, or by some other means. By centralizing the image database, users of the radiographs, such as physicians, nurses, technicians, and other medical professionals at the hospital 104 and the physician's office 110, can gain access to the radiographs without having to store them locally.

In order to transmit this potentially sensitive medical information over the Internet 118, there may be secure connections (e.g., virtual private networks (VPNs) or Secure Sockets Layer (SSL) connections) between the hospital 104 and the server facility 114, as well as between the physician's office 110 and the server facility 114. Alternatively, these VPNs may be between the individual client devices (i.e., the mobile device 102, the table device 106, the PC 108, and the laptop 112) and the server facility 114, or between the individual client devices and the server 116. Thus, as one example, the mobile device 102 may access the server facility 114 via an Internet Protocol Security (IPSec) VPN or some other form of secure connection.

The communication system 110 is intended to be illustrative rather than limiting. Thus, the server facility 114 may be accessed by more or fewer devices from more or fewer physical locations (for instance, a physician may view these images from a hotel room or his or her residence). Thus, there may be thousands of client devices of various types accessing the images from hundreds of locations. Further, the server facility need not be present in a separate physical location. Instead, the server facility may be integrated into one or more of the physical locations of the client devices. Alternatively or additionally, the functions of the server facility may be integrated into the client devices themselves. Moreover, the Internet may be replaced with a private network or may be omitted altogether.

It should be understood that each device depicted in FIG. 1 may be logically or physical distributed over multiple devices of the same type or of a different type. For instance, functions of the server 116 may be distributed across a plurality of server devices, including, but not limited to databases, processing engines, load balancers, and so on. Each of these server devices may be standard PC or server hardware, or customized PC or server hardware. For example, the server 116 may be a rack-mounted or blade server device.

Figure 2:
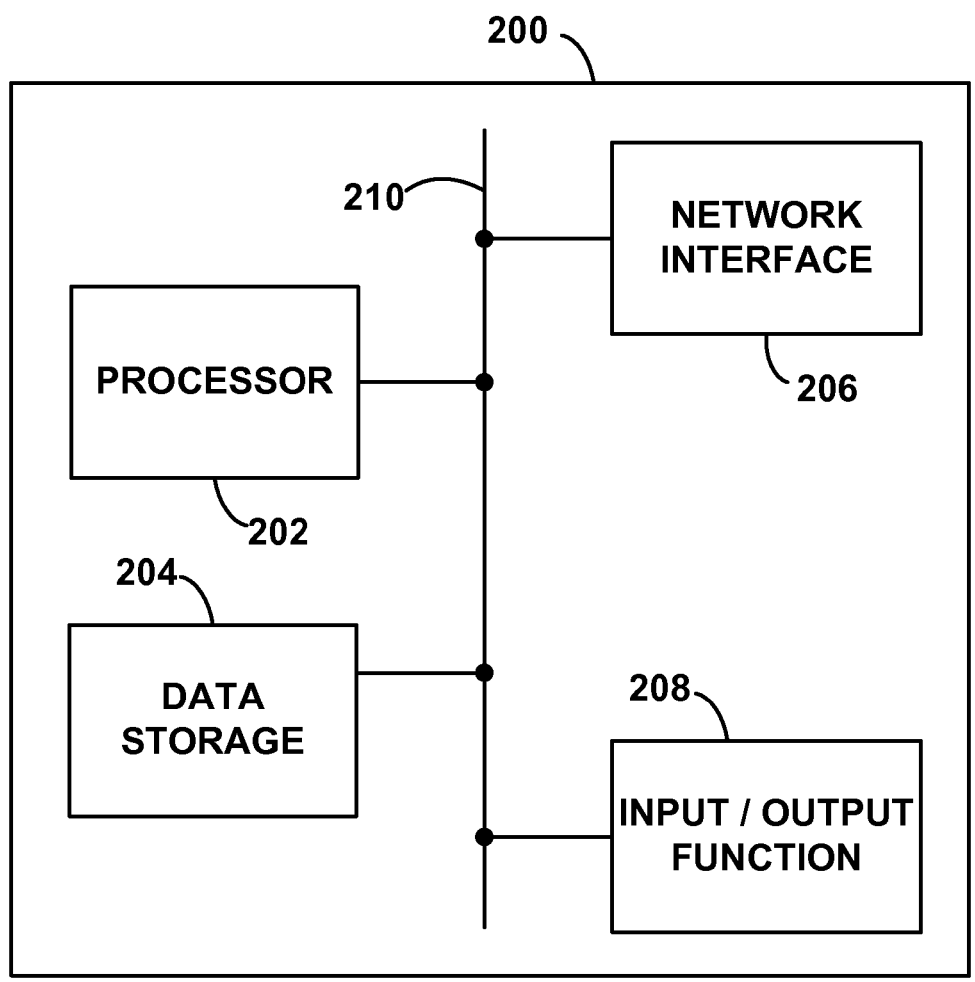
FIG. 2 depicts a block diagram of a computing device that can be used to conduct digital image templating, in accordance with an example embodiment.

FIG. 2 is a simplified block diagram exemplifying the implementation of a device 200 that could be any of the mobile device 102, the tablet device 106, the PC 108, and the laptop 112. FIG. 2 illustrates some of the functional components that would likely be found in such a device arranged to operate in accordance with the embodiments herein.

The device 200 preferably includes a processor 202, a data storage 204, a network interface 206, and an input/output function 208, all of which may be coupled by a system bus 210 or a similar mechanism. The processor 202 preferably includes one or more central processing units (CPUs), such as one or more general purpose processors or one or more dedicated processors (e.g., application specific integrated circuits (ASICs) or digital signal processors (DSPs), etc.) The data storage 204, in turn, may comprise volatile or non-volatile data storage and can be integrated in whole or in part with the processor 202.

The data storage 204 preferably holds program instructions, executable by the processor 202, and data that is manipulated by these instructions, to carry out the various methods, processes, or functions described this specification or the accompanying drawings. Alternatively, these methods, processes, or functions can be defined by hardware, firmware, or any combination of hardware, firmware and software.

The network interface 206 may take the form of a wireline interface, such as an Ethernet, Token Ring, or T-carrier interface. The network interface 206 may also take the form of a wireless interface, such as IEEE 802.11 (Wifi), BLUETOOTH®, or a wide-area wireless interface (e.g., a cellular radio). However, other forms of physical layer connections and other types of standard or proprietary communication protocols may be used over network interface 206. Furthermore, network interface 206 may comprise multiple physical interfaces.

The input/output function 208 may facilitate user interaction with the device 200. Thus, the input/output function 208 may comprise multiple types of input devices, such as a keyboard, a mouse, a touchscreen, and so on. Similarly, the input/output function 208 may comprise multiple types of output devices, such as a monitor, printer, or one or more light emitting diodes (LEDs). Additionally or alternatively, the device 200 may support remote access from another device, via network interface 206 or via another interface (not shown), such a universal serial bus (USB) port.

In combination with, in addition to, or as an alternative to the simplified representation of a computing device found in FIG. 2, any of the methods processes, or functions disclosed in this specification or the accompanying drawings may be represented as program instructions on any appropriate computer-readable medium. Thus, embodiments of this invention encompass an article of manufacture, including a non-transitory computer-readable medium, having program instructions stored thereon that, in response to execution by a computing device, cause the computing device to perform operations comprising any of these methods, processes, or functions.

II. Traditional Templating

Figure 3A:
FIG. 3A depicts the display of a radiograph containing a hip bone structure, in accordance with an example embodiment.
Figure 3B:
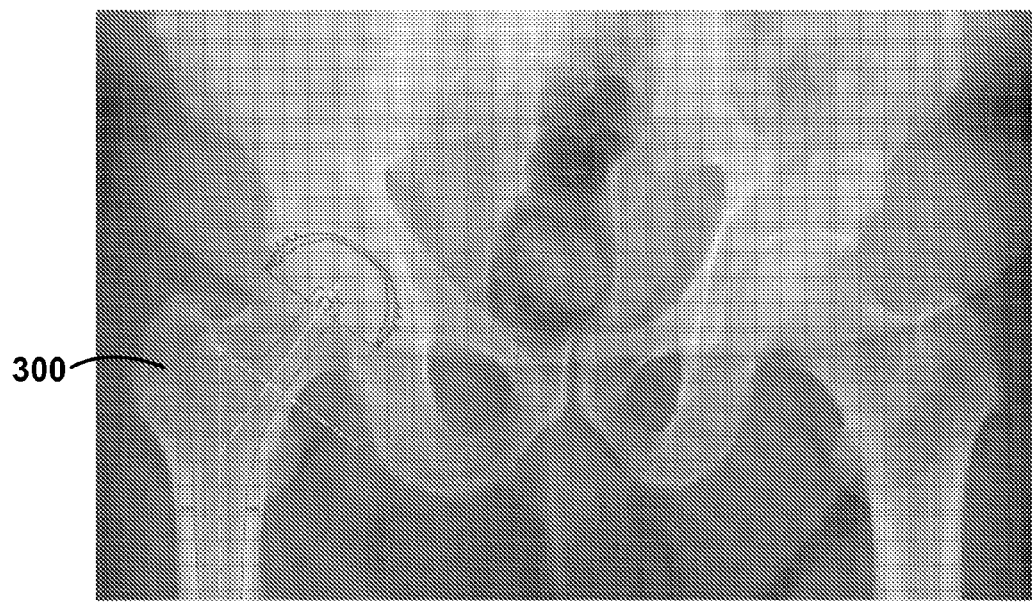
FIG. 3B depicts the display of the radiograph containing a hip bone structure, along with a template of an implant matched to a hip joint to be replaced, in accordance with an example embodiment.

Prior to the widespread use of computers in medicine, implant templating was performed manually. Manual templating typically involves a physician viewing a radiographic film via a projector or placing the radiographic film over a light box so that the radiographic image on the film is illuminated. As shown in FIG. 3A, this illumination may allow the physician to view the bone structure (in this case, a hip) depicted in the radiograph. The physician would also have available a set of clear plastic templates representing implants of various sizes. Each template may represent a particular section of the bone structure. As shown in FIG. 3B, by placing these templates on top of the radiograph, the physician may be able to determine the approximate size of an implant to use with the patient. The physician may rotate or move the template with respect to the radiograph until the physician is satisfied that the template is both of the proper size and aligned with the section of the bone structure it represents.

Templates are typically provided by the manufacturers of implant hardware. Thus, the sizes of the templates may have a one-to-one correspondence with the sizes of implant hardware made by the vendor. Therefore, if a given vendor offers implants in five different sizes, the vendor may also provide templates corresponding to those same five sizes. Each template may represent not only a section of the bone structure (e.g., a joint), but also may include other lines, reference points, markings, or points of attachment that assist the physician in aligning the template with the section of the bone structure.

For example, in FIG. 3B, a physician may arrange a hip joint template with a hip joint depicted in a radiograph until the physician is satisfied with the fit of the template. If the physician is not satisfied with the fit, the physician may choose a template of another size or a template from a different vendor, and repeat the process.

One of the difficulties in traditional templating is that the images depicted in radiographs may be magnified. When a radiograph is taken, an x-ray beam passes through the patient and onto the radiographic film, to produce an image of the patient's bone structure. However, the image of the bone structure may not be equal to the size of the patient's bone, as the image may be magnified. The bone structure's magnification may be proportional to the distance that the bone structure is from the film. As such, if the patient is thin, the bone structure may be closer to the film and the magnification may be small. Conversely, if the patient is muscular or obese, the magnification may be large since the bone may be further from the film. Since there is tremendous variation in human body sizes and shapes, there are correspondingly large variations of magnifications.

In the traditional method of templating, a single set of templates is usually supplied. The templates in the set are based on an estimated average of the magnification in all individuals, since the manufacturer cannot account for all of the variations in image magnification. Thus, the further a patient's body type differs from the estimated average, the templates become more and more inaccurate. Accordingly, orthopedic procedures performed on these patients may have a greater likelihood of complications, since the surgeon, assistant, or sales representative cannot adequately determine what size or type of implant is required. These complications include failure to have the correct hardware at the procedure, intraoperative fracture of bone, failure of the hardware, neurologic injury, chronic pain, or the need for repeat surgery.

In order to overcome this problem, some physicians may place a sizing marker on the radiograph near or at the level of the bone. The marker is preferably of a known size and made from a substance that is visible on radiographs. Using such a radiographic marker enables physicians to more accurately determine the magnification of the bone structure.

However, there are disadvantages to using radiographic markers to assist templating. Although having the radiographic marker in the radiographic image may help the physician determine the magnification level of the bone structure, the physician may not have templates that correspond to this magnification level. Since templating manufacturers cannot account for all the variations in human body habitus and resulting magnifications thereof, surgeons may not have access to the correctly magnified template for each patient. For example, even if a surgeon determines that the magnification of a patient's bone structure is 37%, there will be no template that the surgeon could use to template that bone structure if the templates in the sets are magnified only at 10%, 15%, or 25%.

As a result, some physicians may place an incorrectly magnified template over the bone structure and then adjust the final result by the determined magnification level of the radiograph. However, this method may ultimately fail because the wrong-sized template is used. If the template is not at substantially the same magnification level as the radiograph, it is unlikely that the template can be correctly positioned over the bone structure. If the template is incorrectly positioned over the bone structure, the template cannot be used to adequately determine the final size of the implant. Therefore, using a radiographic marker with traditional templating may not improve the accuracy of the templating process nor reduce the rate of complications.

III. Digital Templating

In order to overcome at least some of the inadequacies of traditional templating, digital templating can be employed. Generally speaking, digital templating involves a digital image of a radiograph depicting a bone structure being shown on a computer screen, along with a digital representation of a template. Via a computer interface, a physician may be able to size, rotate, or move the representation of the template so that it is aligned with the at least a section of the bone structure. In this way, the physician is able to perform orthopedic templating from virtually any computer device.

To that point, the communication system 100 of FIG. 1 is a suitable architecture for digital templating. In particular, many medical imaging systems use the Picture Archiving and Communication System (PACS) hardware and software.

PACS is designed for storage, management, and access to digital images, and is used primarily by the medical community. Thus, many medical devices, such as magnetic resonance imaging (MRI), ultrasound, and x-ray machines are integrated to some extent with PACS. PACS uses the Digital Imaging and Communications in Medicine (DICOM) format for the storage and communication of these images. A goal of standardizing upon PACS and DICOM is to allow medical professionals to be able to securely store, view, and share digital images. For instance the server 116 could be a PACS server, and each of the client devices may include PACS client software.

Given the trend in recent years toward digital imaging in the medical profession, PACS use has become widespread to the point that it is virtually required in some practices. In response to this demand, many hardware and software vendors have developed PACS compatible devices and applications. For instance, there are a wide variety of PACS clients available for PCs running MICROSOFT® or APPLE® operating systems.

However, while using a system like PACS has advantages, doing so also has significant shortcomings. PACS systems can be prohibitively expensive. For instance, a physician in a small or medium sized practice may be reluctant to spend the initial capital required to install PACS hardware or software in the practice. Additionally, the PACS vendor may also charge regular maintenance or service fees for access to the PACS server. Further, due to PACS clients typically being in communication with PACS servers via the Internet, the transfer and manipulation of large images can be slow, and slow response times can lead to user frustration.

Moreover, physicians tend to be busy professionals, and may not have much computer experience. Thus, as a general rule, physicians want their computer applications to "just work." As a result, they may not have the patience to learn the full capabilities of a PACS client user interface, especially since these physicians are likely to already be comfortable with manual methods of orthopedic templating. Further, as the physician moves between client devices that use different PACS client software, the physician may not want to have to learn multiple user interfaces. Even if the physician is comfortable with using more than one PACS client, each PACS client may require configuration of a VPN to a different PACS server facility. For small practices, the physicians and their staff may not have the information technology (IT) expertise to set up these VPNs, and may not have the budget to hire part or full time IT professionals to configure and maintain VPNs.

Another disadvantage to using PACS clients for digital templating is that it has proven difficult for implant vendors to integrate their templates into PACS client software packages. Implant vendors and PACS client software vendors may be different entities. Thus, in order for an implant vendor to have their implants included in multiple PACS client software packages, the implant vendor may have to reach business arrangements with each of the PACS software vendors. Even if the implant vendor is able make these arrangements, the implant vendor would still have to integrate their templating specifications into the potentially disparate software architectures of each PACS client. As a result of this difficulty, implant vendors may support only their own proprietary PACS clients. Consequently, physicians may need to use multiple PACS clients in order to perform digital templating, leading to additional cost and frustration.

Typically, templating software is implemented into PACS in several ways. Using one method, a templating software vendor may integrate the templating software within their proprietary PACS software clients. The templating software can only be used with their proprietary PACS client and requires the user to purchase their PACS solution including the hardware and software, in addition to the templating software. This can be prohibitively expensive and require physicians to repurchase an entirely new system including PACS hardware, PACS software, and templating software just to be able to perform templating. Furthermore, the physician may be "locked" into the vendor's system and cannot choose "best-of-breed" components or modules without changing to or purchasing an expensive new system.

Other vendors offer a solution to this problem. Some templating vendors specialize in integrating templating within other PACS vendors' software. In this fashion, they can offer templating to those physician practices that already have an established PACS system. This potentially eliminates the need for the practice to invest in an entirely new system. However, this method also has significant drawbacks, as integration with each separate PACS vendor's proprietary software is both time-consuming and expensive for the templating vendor, and this significant cost is passed onto the physician's practice. Furthermore, changes in the proprietary PACS systems of the physician require a corresponding update in the templating software with expensive reprogramming. Moreover, templating vendors are unlikely to be able to integrate within all proprietary PACS systems as there are literally hundreds of systems.

Another option may be offered by templating vendors. In order to eliminate the time consuming and costly integration of their software within proprietary PACS software, they will integrate their own templating software within their own proprietary PACS client. This PACS client is then integrated within users' existing PACS network either locally or as a server that can be accessed via an Internet connection.

Nonetheless, there are several problems with this solution. In particular, it requires that users learn two different PACS clients—one for day-to-day use and another for templating. As these PACS clients are complex, the user may effectively have to re-learn the templating application with each use. This is especially frustrating for users that are used to the relative simplicity of traditional templating. Additionally, requiring an Internet-based solution can lead to the templating application to respond slowly when there is network congestion, and potentially to be unavailable when network connectivity is down.

Moreover, this method only moved costs, it did not decrease costs. Although costs associated with PACS software integration may have been eliminated, costly network integration and support may be required. The templating vendor must now work to integrate their system into the multiple complex networks used by physicians. For example, a typical orthopedic physician works at multiple hospitals and surgery centers, each with their own information technology department and unique network and VPN security settings. The physician also has their unique network which may include more than one office, an imaging unit, and a surgery center. The templating vendor must work with the physician's information technology department to integrate within this network as well. This may be time consuming and expensive, and this cost may be passed onto the physician. Unfortunately, the costs do not end there, as the templating vendor may require costly annual maintenance fees to support this network and integration. For example, any time the PACS network or VPN settings change, the templating software could require a corresponding change, resulting in maintenance work by the vendor.

Figure 4:
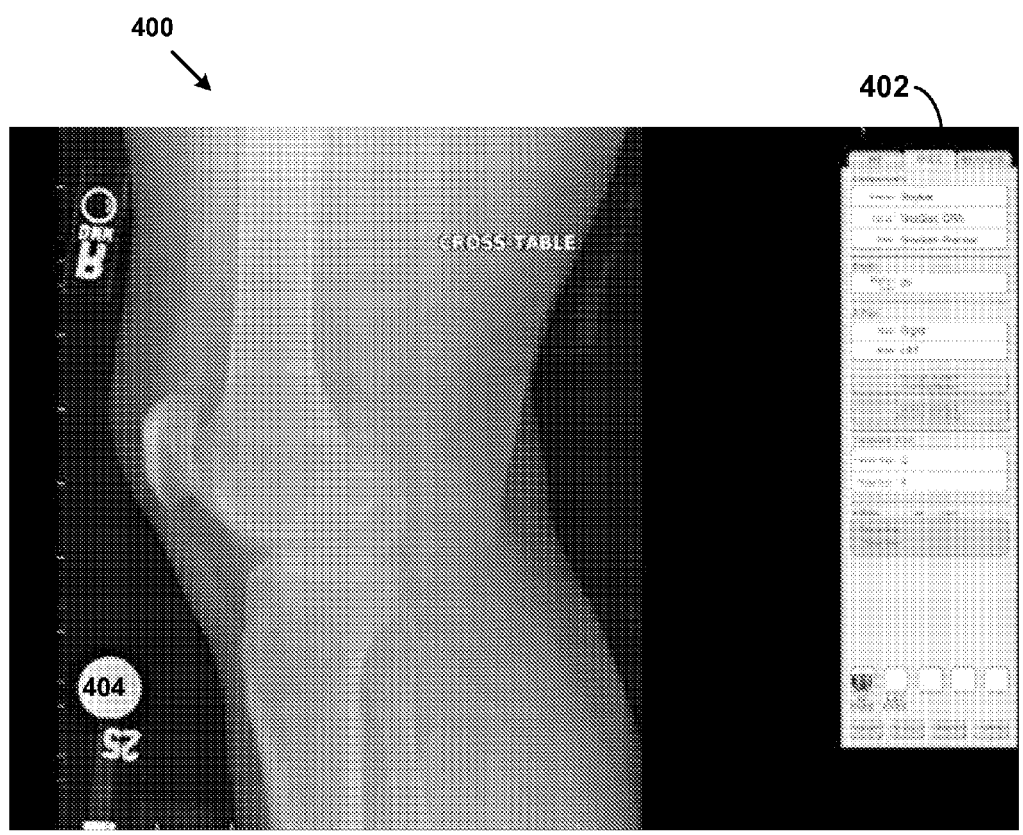
FIG. 4 depicts the display of a radiograph via an image viewing application, as well as the display of a user interface of a templating application, in accordance with an example embodiment.

FIG. 4 depicts an embodiment that addresses both these technical and business obstacles. In particular, FIG. 4 includes a digitally-displayed radiograph 400 of a knee bone structure. The application that displays the radiograph 400 may be, for instance, a PACS client, or some other type of image viewer. In addition to the bone structure, the radiograph may also display a radiographic marker 404. On top or alongside the display of radiograph 400, the user interface of a templating application 402 may be displayed.

Preferably, the templating application is independent of the application that displays the radiograph 400. This independence could be exhibited in a number of ways. For instance, these two applications could take the form of two different executable files that were separately compiled. As such, these applications might not share memory or code with one another. Further, these applications might not communicate with one another. However, it is well-known in the art that two applications can share common object code or library code, such as dynamically-linked libraries (DLLs) or other forms of shared libraries, without losing their independence from one another.

In an optional embodiment, the templating application may perform or trigger a screen capture operation of the display of the radiograph 400. It should be understood that a screen capture operation may cause an image of this display to be recorded. Thus, for instance, the templating application may make a copy of some or all parts of the output on the computer screen. Then, the templating application may read, use, or manipulate this copy when performing templating functions. Doing so allows a further degree of independence between the templating application and the application that displays the radiograph 400. Particularly, once the screen capture is performed, the radiograph 400 can be resized, moved, closed, or deleted without impacting the templating application. This screen capture can be performed upon initiation of the templating application, or at any other time during the course of templating. Nonetheless, performing a screen capture is not a necessary step of templating, and templating can be conducted without performance of screen captures.

In another optional embodiment, the templating application could take the form of a "widget" or a "gadget." For example, a widget for the MAC OS® operating system is an application that is not displayed to the user until the user activates the widget (e.g., with a keystroke or by some other means). Once activated, the widget may appear in the foreground, either with background applications dimmed, or by transparently or semi-transparently overlaying these applications. An activated widget may be able to be moved, rearranged, de-activated, or deleted. Typically, widgets perform simple tasks such as clock, weather, and calendar functions, but in full generality, widgets can perform any tasks that a standard computer application could perform. Widgets may be associated with some form of dashboard, launcher, or sidebar so that the user has easy access to initiating and using the widget.

Widgets are similar in concept to the gadgets of MICROSOFT WINDOWS VISTA® and WINDOWS 7®, as well as other types of user interface constructs available on other operating systems and graphical user interfaces. Thus, the use of widgets is not confined to such MICROSOFT® or APPLE® operating systems, and may be used with other types of operating systems as well.

The programming environment used to create widgets may be standard or proprietary. For instance, some widgets could be created through use of standard HyperText Markup Language (HTML), Cascading Style Sheets (CSS), or JavaScript. On the other hand proprietary schemes such as ADOBE AIR®, ADOBE® Flash or SILVERLIGHT® could also be used. Of course, the templating application 402 could be based on other tools, platforms, or technologies as well.

Regardless of how it is implemented, the templating application 402 preferably comprises one or more tabs, text boxes, sliders, radio buttons, menus or other user interface components that allow the user to perform at least one of the following functions: (a) measuring the size of the radiographic marker 404 in the radiograph 400, (b) selecting a template that represents an implant of a particular manufacturer and size, or (c) rotating or moving the selected template so that the template and at least a section of the bone structure depicted by the radiograph 400 are overlaid. Of course, the templating application 402 may contain logic, in the form of program instructions, to perform these functions. For example, this logic may perform measurements of simple lengths, diameters, and angles. The logic may also perform more complex measurements requiring a combination of measurements, calculations and comparisons. Further, the templating application 402 may be able to perform additional functions not explicitly discussed herein.

As discussed above, the radiographic marker 404 may be measured. One way of accomplishing this goal is for the templating application 402 to allow the user to specify the location of reference points associated with the radiographic marker 404. For instance, the user may select the radiographic marker 404 with a mouse pointer or a touchscreen input device, and thereby specify its radius, diameter, or outline. In doing so, the templating application 402 may mark this radius, diameter, or outline on the screen with one or more points, lines, or other indicia. Of course, the templating application 402 may include functions for automatically detecting and specifying the radiographic marker 404.

Once the radiographic marker 404 has been specified, its virtual size may be measured. Preferably, the virtual size of an object displayed on a computer screen can be represented by the size of the object as shown on the screen. For instance, if the radiographic marker 404 is 25 millimeters in diameter, but is displayed with a diameter of 50 millimeters, then its magnification level is 100% (the size of the radiographic marker 404 has been doubled). The virtual size of an object can also be measured by the number of pixels used in the geometry of the radiographic marker 404.

As is known in the art, a pixel (a shortened version of the term "picture element") may refer to a dot-like point displayed on two-dimensional grid. Typically, the grid appears on a computer screen. By lighting, or turning on, various pixels with appropriate colors, images can be formed on the computer screen. As or after the templating application 402 marks the radius, diameter, or outline of the radiographic marker 404, the templating application 402 may determine the approximate or exact number of vertical or horizontal pixels in the display of the radiographic marker 404. This number can then be used in various ways to determine the actual size of the bone structure depicted in the radiograph.

For instance, if the radiographic marker 404 is known to be 25 millimeters in diameter, and the templating application determines that there are 75 pixels in the display of the radiographic marker 404, then the templating application 402 has also determined that the radiograph depicts the image at a ratio of three pixels per millimeter. Then, the templating application 402 can shrink or expand the displayed sizes of templates in order to match this ratio. Thus, if a particular implant has an axial length of 300 millimeters, the templating application 402 may display the corresponding template of the implant using 900 pixels to represent the implant's axial length. In this way, the template is displayed at approximately the same scale as the bone structure, resulting in a better matching of the template to the bone structure.

In order to facilitate this functionality, the templating application 402 may contain or have access to one or more a template libraries. Each template library may contain one or more templates from a given implant vendor. Preferably, each implant size for a given piece of implant hardware is represented with a template in the template library. The templating application 402 may allow the user to search for or select a template by medical procedure, implant vendor, or size. In addition to including implants of different sizes, templates of different shapes and designs may also be included in these databases, and these templates may also be chosen by the user. Once a template is chosen and scaled according to the measured size of the reference object, the template may be displayed in conjunction with the bone structure.

Figure 5A:
FIG. 5A depicts the fitting of a digital template to a radiographic image of a bone structure, in accordance with an example embodiment.

FIG. 5A depicts the placement of a template 500 on the radiograph 400. In this case, the template 500 represents part of an implant for replacing a knee. As shown in FIG. 5A, the template 500 may be displayed transparently or semi-transparently so that it can be matched to a section of the bone structure. Alternatively, the bone structure may be displayed transparently or semi-transparently instead.

Also as shown in FIG. 5A, the template 500 is not completely in place. Therefore, the templating application 402 (which is not shown in FIG. 5A in order to focus on the fit of the template to the bone structure) may allow the user to rotate or move the template 500 so that the template 500 substantially aligns with at least a section of the bone structure. Alternatively, the templating application 402 may automatically perform rotation or movement on behalf of the user, or may suggest rotation or movement to the user.

Further, in orthopedic procedures to stabilize bone fractures, templates may be used to size plates, rods, screws, or pins that may be attached to or placed within fractured bones. In order to properly align such templates, the templating application may also allow the user to twist or bend the template 500 so that the template 500 substantially aligns with at least a section of the bone structure. In other orthopedic procedures, hardware may also be used to stabilize bone structures following a bone cut. This typically may be done during corrective procedures to improve bone alignment.

In some orthopedic procedures, more than one template may be used. Thus, a similar series of steps to scale, select, rotate, and move each template may be performed. Moreover, the templating application may allow the user to specify how and where these templates may be connected or may interact with one another.

Regardless, once the user is satisfied with the size and alignment of the template 500, the user may indicate as such to the templating application 402, and the templating application 402 may indicate or record characteristics of the template 500 (e.g., the make, model, brand or size of the template 500). Additionally, the templating application 402 may associate these characteristics with the radiographic image 400, or with the patient of whom the radiographic image 400 was taken.

Use of the templating application 402 has a number of advantages over other methods of templating. The templating application 402 does not require the costly and complex integration required with PACS-based templating solutions. Thus, the templating application 402 does not need to be integrated and maintained within proprietary PACs software or within multiple complex networks, significantly reducing both cost and time to implementation.

The templating application 402 also enables the user to select a best-of-breed PACS system that best suits their needs, not just a PACS system that allows the user to perform templating. Additionally, the templating application 402 may prevent the user from having to repurchase an entirely new PACS system. Moreover, the user may modify or upgrade a PACS system without having to worry about costly system upgrades, changes, or downtime due to the PACS system's integration with the templating application 402.

In addition, by performing digital templating with a templating application that is independent from the application that displays the radiograph, the templating application can be used with any such image display application. Thus, templating application 402 could be used not only with any PACS client, but also with email applications, messaging applications, web browsing applications, file transfer applications, or image viewing applications. Further, since a PACS client is not required to perform the templating procedures, a VPN or other form of secure connection need not be in place. Thus, for example, the user of the templating application 402 may receive a radiograph via email and then perform templating with the radiograph as displayed in his or her email client application. With the radiograph stored and manipulated locally on the user's computer, the delays and slowness associated with secure network access and large file size can be avoided. Further, the independence of the templating application 402 from the application that displays the radiograph may also result in users only having to learn one templating application user interface. This may save time and reduce user frustration.

However, any independence of the templating application from the image viewing application does not imply that the templating application cannot communicate with other networked devices. For example, the templating application may send and receive radiographic images from one or more servers that store these images in a centralized or distributed fashion. This arrangement facilitates communication between surgeons, assistants, sales representatives, and so on.

Figure 5B:
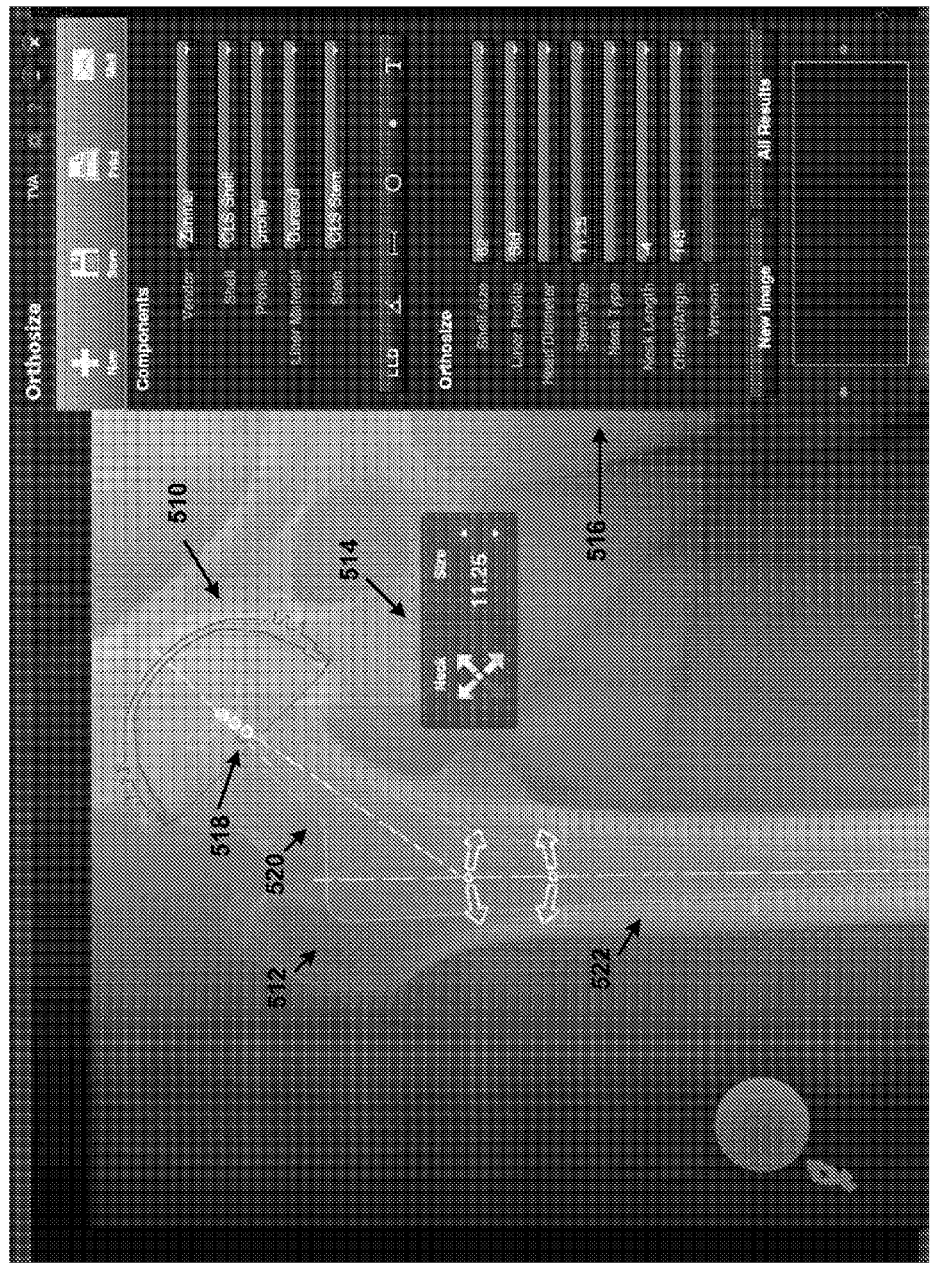
FIG. 5B also depicts the fitting of a digital template to a radiographic image of a bone structure, in accordance with an example embodiment.

FIG. 5B depicts an illustrative graphical user interface design for placement of templates on a radiographic image. Although FIG. 5B shows templating for a hip replacement procedure, the general approach shown in FIG. 5B can be applied to other procedures as well. This optional interface design advantageously allows the manipulation of a shell template 510 and a stem template 512, as well as their relationship with one another, via a heads up display 514. Preferably, the heads up display 514 comprises a form of floating dialog box that appears somewhat near the shell template 510 and the stem template 512. The heads up display 514 may be modeless so that its presence does not block the user from interacting with other parts of the templating application 516 or other applications.

Rather than requiring the user to manipulate each object from one or more drop-down menus (or other types of selection mechanisms) in the templating application 516, the heads up display 514 (which may be considered part of the templating application 516) allows the user to specify the shell template 510 and the stem template 512 via a simplified user interface. In particular, the user may specify the size, length, and offset of the shell template 510. Likewise, the user may manipulate length of the neck 520 and size of the stem 522 of the stem template 512, as well as the stem angle, offset and version. Any size changes may be depicted by the user interface changing the display sizes of the shell template 510 or the stem template 512. Neck length, offset, and version changes may be represented by the connection points 518 for the shell template 510 or the stem template 512. Once these points are positioned either through the use of the heads up display 514 or other user interface components, the computing device may perform several calculations including changes in leg length and offset.

For hip replacement procedures, offset may be defined as the horizontal distance between the final head position of the implant and the shaft of the femur, while leg length may be defined as the vertical distance. This vertical and horizontal distance may be made larger or smaller to optimize postoperative hip biomechanics. The heads up display 514 may allow the user to fine tune the postoperative leg length and offset to prevent postoperative nerve injury, limp, hip instability, and pain. For other types of orthopedic procedures, offset may take on other definitions.

For instance, the user may choose the shell template 510, and then place, size, or align this template on the radiographic image so that the shell template 510 substantially matches the hip socket depicted in the radiographic image. The procedure may also involve the user choosing the stem template 512, and then placing, sizing, and aligning this template on the radiographic image so that the stem template 512 substantially matches the leg bone depicted in the radiographic image. Advantageously, some or all of these steps may be performed via the heads up display 514, so that the user does not need to refer back and forth between the templates and the drop down menus of templating application 516.

The heads up display 514 may also facilitate the positioning of the shell template 510 and the stem template 512 with one another. Such positioning may influence the patient's post-operation leg length and offset. Thus, for instance, the heads up display 514 may allow the user to select the connecting points 518 on either or both of the shell template 510 and the stem template 512. By selecting one of several such points, the alignment of the shell template 510 and the stem template 512 may be chosen to provide a desired leg length or offset.

Of course, any of the procedures shown in FIGS. 5A and 5B are for purposes of example, and are non-limiting. Thus, the embodiments herein may be applied to other types of orthopedic procedures, as well as to non-orthopedic procedures. Further, any of the steps described with respect to these figures may be automated in whole or in part.

Figure 7:
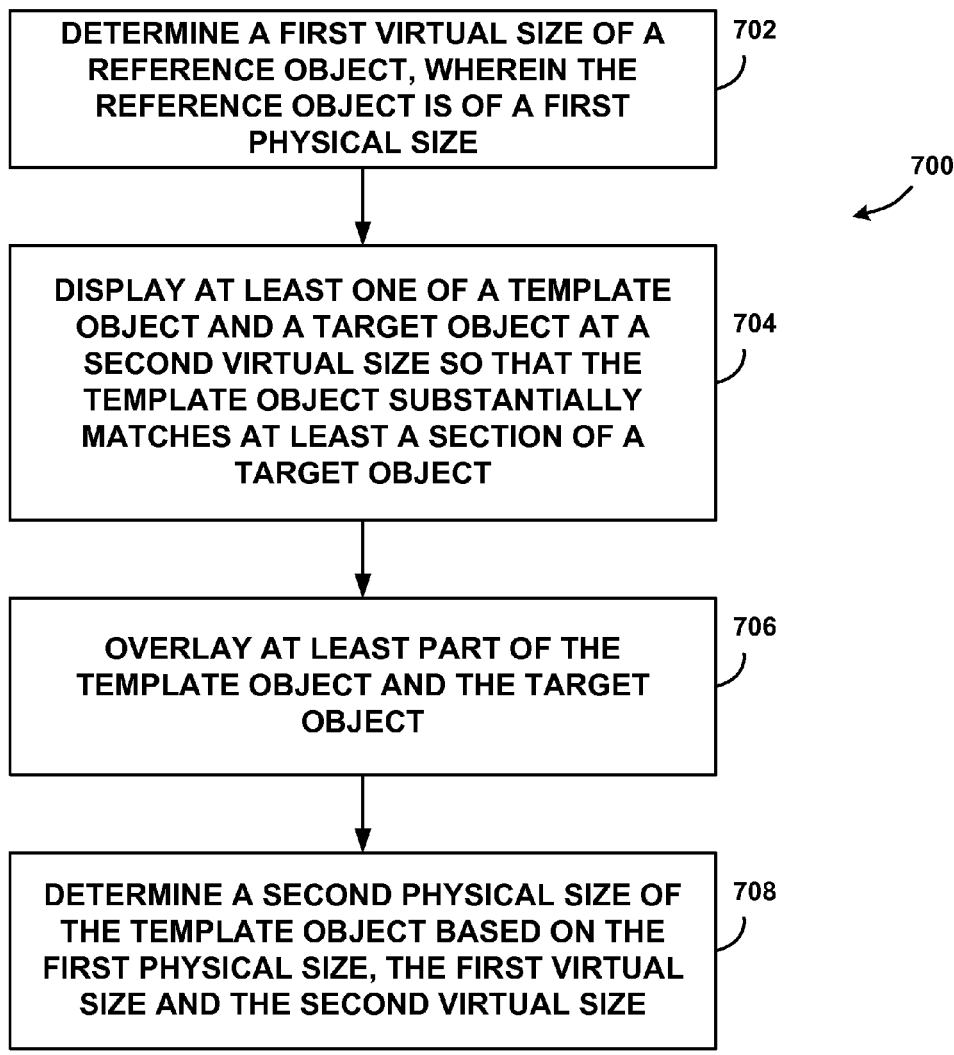
FIG. 7 is a second flow chart, in accordance with an example embodiment.

FIGS. 6 and 7 are flow charts 600 and 700, respectively, of example embodiments for digital templating. It should be understood that, for each of these flow charts, more or fewer steps may be used. Thus, for example, steps may be added to or omitted from flow chart 600 or flow chart 700. Further, the ordering of the steps in each flow chart is for purposes of example, and other orders of steps may be used. Additionally, flow charts 600 and 700 may be combined with one another, in whole or in part, without departing from the scope of the invention. Thus, as a whole, it should be understood that these flow charts are intended to be illustrative rather than limiting.

Flow chart 600 is arranged according to an example embodiment. At step 602, a template object is displayed on an output device that is also displaying a target object and a reference object. The target object may depict a radiographic picture of a bone structure, and the template object may represent a replacement part for the bone structure or a stabilization implant for the bone structure. The target object and reference object may be displayed at an initially unknown magnification level, or scale. Preferably, the reference object is of a known size. Thus, by measuring the size of the reference object as displayed, the magnification level can be discovered.

At step 604, based on the measured size of the reference object, at least one of the template object and the target object may be adjusted from a first size to a second size such that the template object substantially matches at least a section of the target object. At step 606, the template object may be overlaid on or with the target object. This overlaying may occur before or after the template object or the target object is adjusted from the first size to the second size. Additionally, the overlaying may involve displaying the template object or the target object in a transparent or semi-transparent fashion.

If the template object is sized, the first size may be chosen from a range of sizes. Each size in this range may correspond to a particular model, brand, or make of implant hardware. Further, the first and second sizes may have any relation to one another. For instance, the first size may be smaller than the second size or vice versa.

Moreover, the template object may be displayed by a first application, and the reference object and the target object may be displayed by a second application. In other words, the first and second applications may be independent of one another. Preferably, the first application does not have access to program instructions or memory used by the second application. Additionally, the first application may not be able to communicate with the second application.

At steps 608 and 610, the template object may be rotated and moved, respectively, so that it aligns with at least the matched part of the target object. Alternatively, the target object may be rotated or moved to achieve the same goal. Once the user is satisfied with the size and alignment of the template object, the first application may store or otherwise record the template object's size, as well as other information that may be provided. It should be noted that steps 608 and 610 may occur in any order. Thus, the template object may be rotated then moved, or moved then rotated.

Flow chart 700 is arranged according to another example embodiment. At step 702, a first virtual size of a reference object is determined. Preferably, the reference object is of a first physical size that is known, and the reference object was previously displayed on a computer screen. Thus, the first virtual size of the reference object may be expressed as a number of pixels. In this way, the magnification level of the reference object, which can be expressed as a ratio of pixels per millimeter (or any other unit of measure), can be determined.

At step 704, at least one of a template object and a target object is displayed at a second virtual size so that the template object substantially matches at least a section of the target object. The target object may have been previously displayed on the computer screen at the same magnification level as the reference object, and may be a radiographic picture depicting a bone structure. Preferably, the second virtual size is based on the determined magnification level. For example, given the ratio of pixels per millimeter, the second virtual size can be based on the number of pixels required to display the template object at the same magnification level at which the target object is displayed. If the template object is displayed at the second virtual size, then preferably the second virtual size of the template object is chosen from a discrete range of virtual sizes, where each of these virtual sizes may correspond to a particular make, model, brand, or size of implant hardware.

At step 706, at least part of the template object is overlaid on or with the target object. This overlaying may include displaying the template object or the target object in a transparent or semi-transparent fashion. Although not shown in FIG. 7, the template object may also be rotated or moved to substantially align at least part of the template object with the matched section of the target object.

At step 708, a second physical size of the template object may be determined based on the first physical size, the first virtual size and the second virtual size. Preferably, the second physical size is determined by applying the magnification level to the second virtual size in order to determine the ratio of millimeters per pixel (or any other unit of measure) for the displayed target object.

As described in the context of flow chart 600, the template object may be displayed by a first application, and the reference object and the target object may be displayed by a second application. Thus, the first and second applications may be independent of one another such that the first application does not have access to program instructions or memory used by the second application. Additionally, the first application may not be able to communicate with the second application.

IV. Further Aspects of Digital Templating

FIGS. 8A, 8B, 8C, 8D, 8E, 8F, and 8G each depict one or more steps of additional example methods for fitting a template image to a target image. The template image may depict, for example, at least part of an artificial joint, and the target image may represent at least part of a bone structure that the artificial joint is meant to replace, stabilize, or otherwise interact with.

According to some aspects of these methods, a displayed template image may be oriented to substantially fit with at least part of a displayed target image. As part of this orientation and fitting process, the user may scale (e.g., magnify) the template image to any one of a virtually infinite number of possible template scales. These scales may be limited by the screen resolution (e.g., the number and size of pixels) of the computing device's output. However, as discussed above, the physical sizes of actual joint replacement hardware may be limited to a relatively small, discrete range of sizes.

Thus, the computing device may then select a physical size from a discrete range of physical sizes. This selection may be made so that, out of the physical sizes in the discrete range, the actual joint replacement of the selected physical size is a closest match to the adjusted scale of the displayed target image.

Figure 8A:
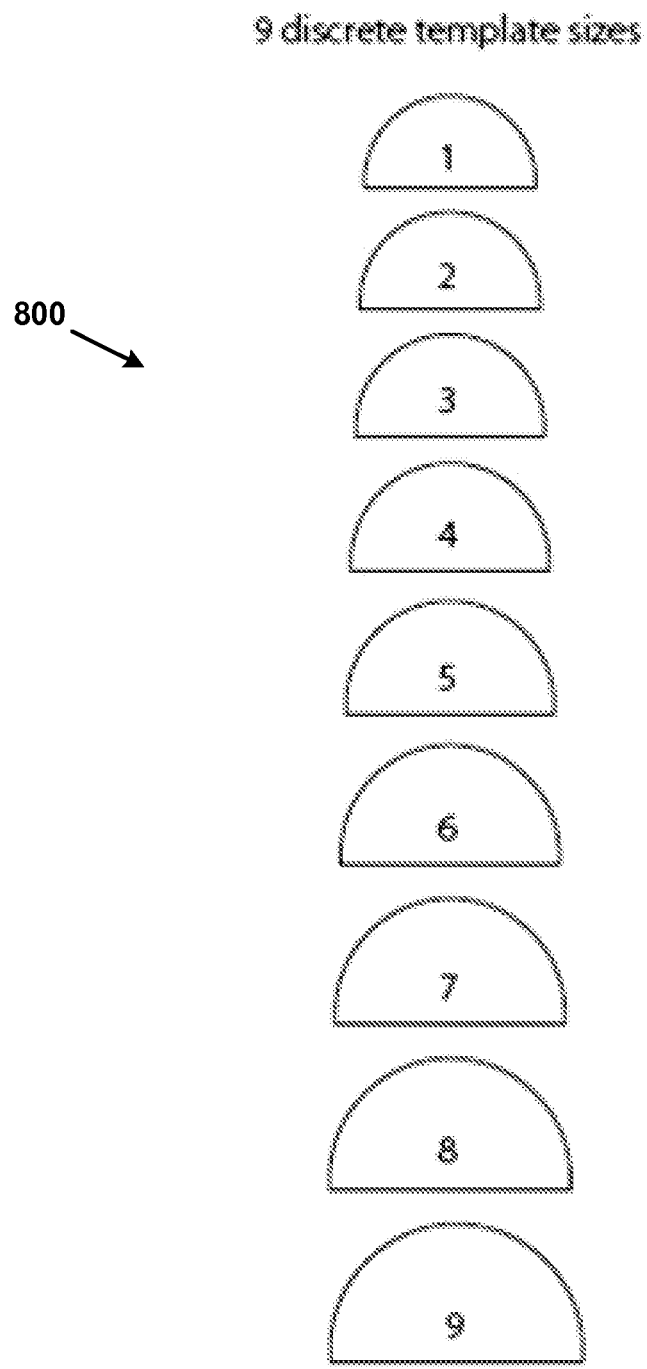
FIGS. 8A, 8B, 8C, 8D, 8E, 8F, and 8G each depict one or more steps of a process for fitting a template image to a target image, in accordance with an example embodiment.

In FIG. 8A, 9 discrete template sizes 800 are shown. These templates may represent, for instance, the socket component of a ball-and-socket joint. Each of the 9 discrete template sizes 800 is of a different size, and numbered from 1 to 9 in order of increasing size. Thus, template size 1 is smaller than template size 2, template size 2 is smaller than template size 3, and so on. In some embodiments, more or fewer that 9 template sizes may be available.

Each of these template sizes may correspond to a physical joint replacement part size that could be surgically implanted into a patient in, for example, a hip replacement procedure. Thus, the 9 discrete template sizes 800 may represent 9 actual replacement joint sizes that a physician would choose from in order to determine the size of a replacement joint to use in a particular procedure. The actual joint replacement parts may come from a single vendor or from multiple vendors.

Figure 8B:
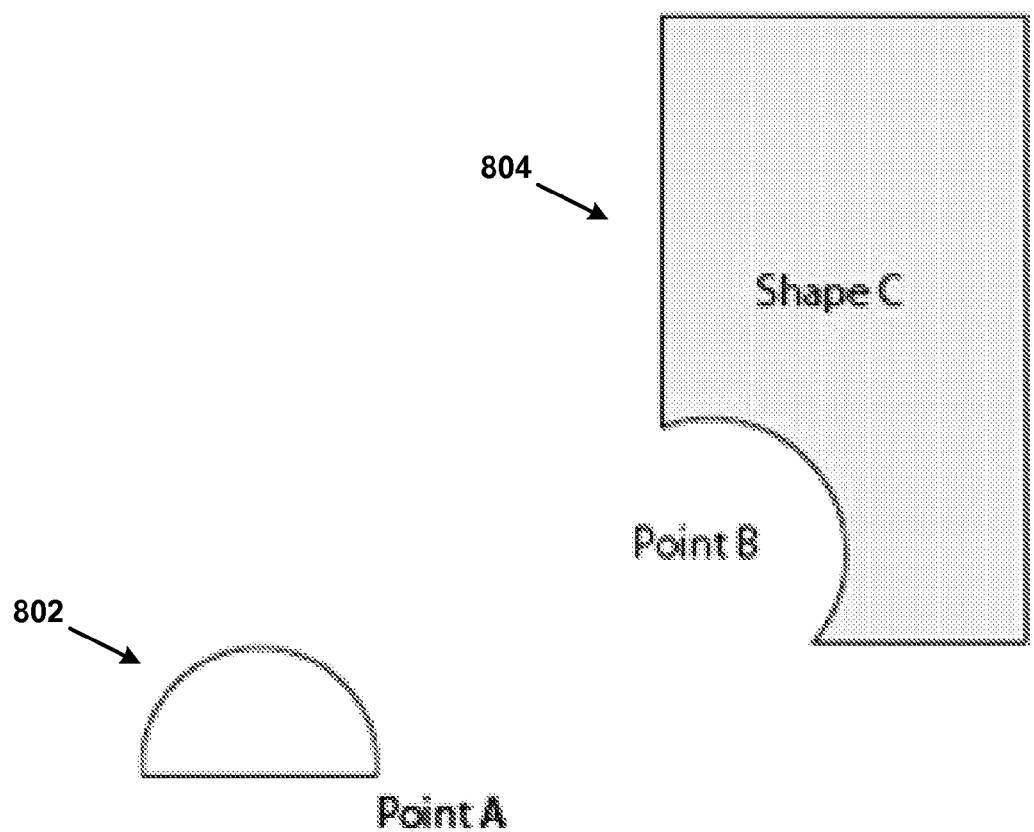

FIG. 8B depicts a template image 802 being displayed with a target image 804. While the target image 804 is a simplified "Shape C" for purposes of example, in orthopedic joint replacement procedures, the target image 804 would likely represent a bone structure.

In at least some instances, the user's goal is to fit the convex portion of the template image 802 to the concave "Point B" of the target image 804. The user may pursue this goal through a combination of scaling, rotating, and/or positioning the template image 802 with respect to the target image 804.

Figure 8C:
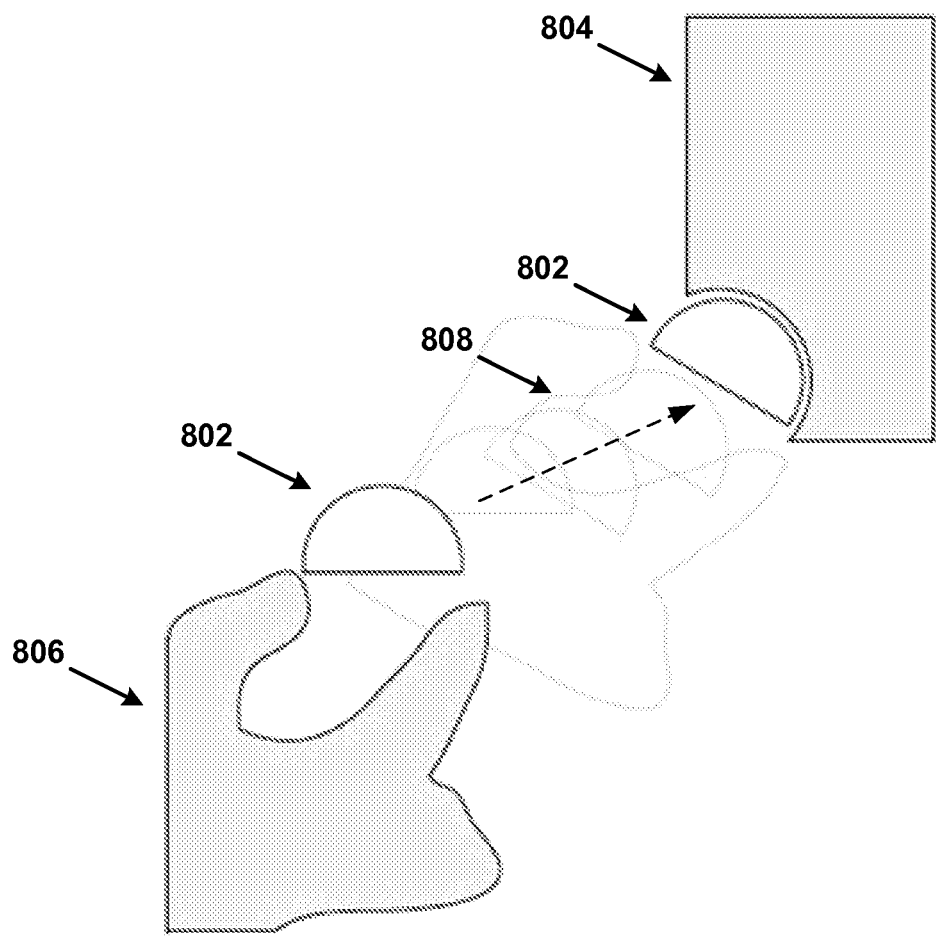

To that end, FIG. 8C depicts the template image 802 being positioned and rotated to fit into the target image 804. In particular, FIG. 8C depicts the template image and the target image 804 being displayed on a touchscreen interface, and a hand 806 using a multitouch gesture on the touchscreen to perform the positioning and rotation.

For instance, the user may place his or her index finger on one part of the template image 802 as displayed on the touchscreen, and also place his or her thumb on another part of the template image 802 as displayed on the touchscreen. Then, maintaining these points of contact with the touchscreen, the user may slide his or her index finger and thumb along the touchscreen, and the touchscreen may depict the template image 802 being "dragged" 808 from one point to another.

Similarly, the user may rotate the position of his or her index finger and/or thumb on the touch screen, and the touchscreen may display the template image 802 being rotated accordingly. The axis of the rotation may be either the user's index finger or thumb. Alternatively, if the user rotates the position of both of his or her index finger and thumb, the axis of rotation may be a different location.

Touchscreen devices may have additional advantages for digital templating. For example, popular types of tablet computers often include an integrated camera. In some embodiments, this camera may be used to directly or indirectly capture the target image. For instance, the user can take a picture of a radiograph with a table computer's camera, and then fit a template image to this captured radiograph. Nonetheless, it should be understood that use of a touchscreen, as well as use of multitouch features, are not required with the embodiments herein. Thus, other types and arrangements of input may be used instead.

Figure 8D:
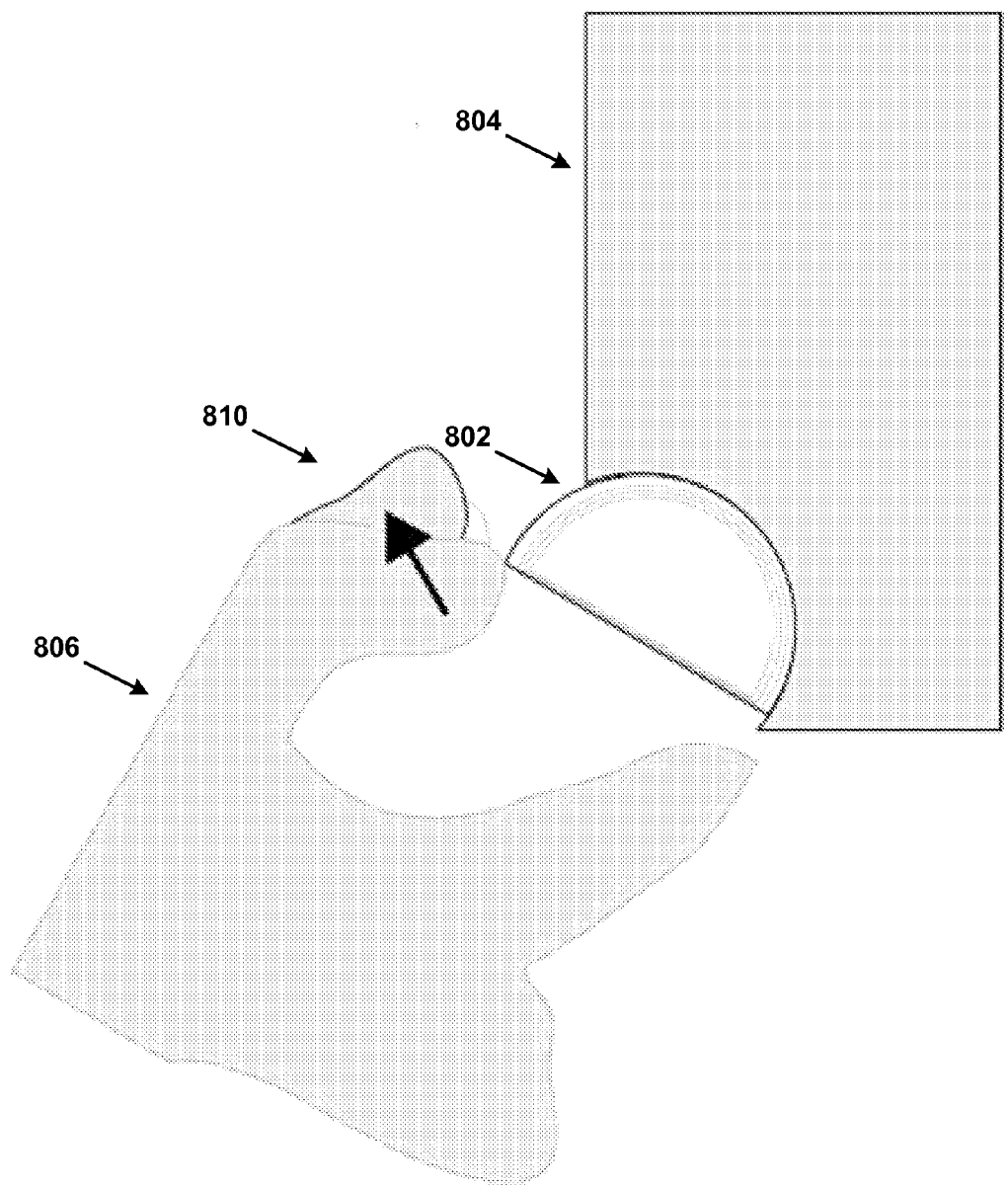

FIG. 8D depicts the user scaling the positioned and rotated template image 802. The user may use a "reverse pinch" gesture to increase (magnify) the scale of the template image 802. Additionally or alternatively, the user may use a "pinch" gesture to decrease (de-magnify) the scale of the template image 802. For example, in FIG. 8D, the user spreads his or her index finger and thumb further apart in a reverse pinch gesture 810 to increase the scale of the template image 802. Through the course or one or more such pinch and/or reverse pinch gestures, the template image 802 may be made to substantially fit part of the target image 804.

In some situations, two or more acts of positioning, rotation and scaling may occur simultaneously or substantially simultaneously. For instance, while dragging 808 the template image 802 to the target image 804, the user may also rotate and/or scale the template image 802, as part of the same gesture. Additionally, the positioning, rotating, and/or scaling may occur in more than one set of continuous gestures. For example, the user may position and rotate the template image 802, lift his or her fingers from the touchscreen, and then depress his or her fingers on the touchscreen again to scale the template image 802.

Figure 8E:
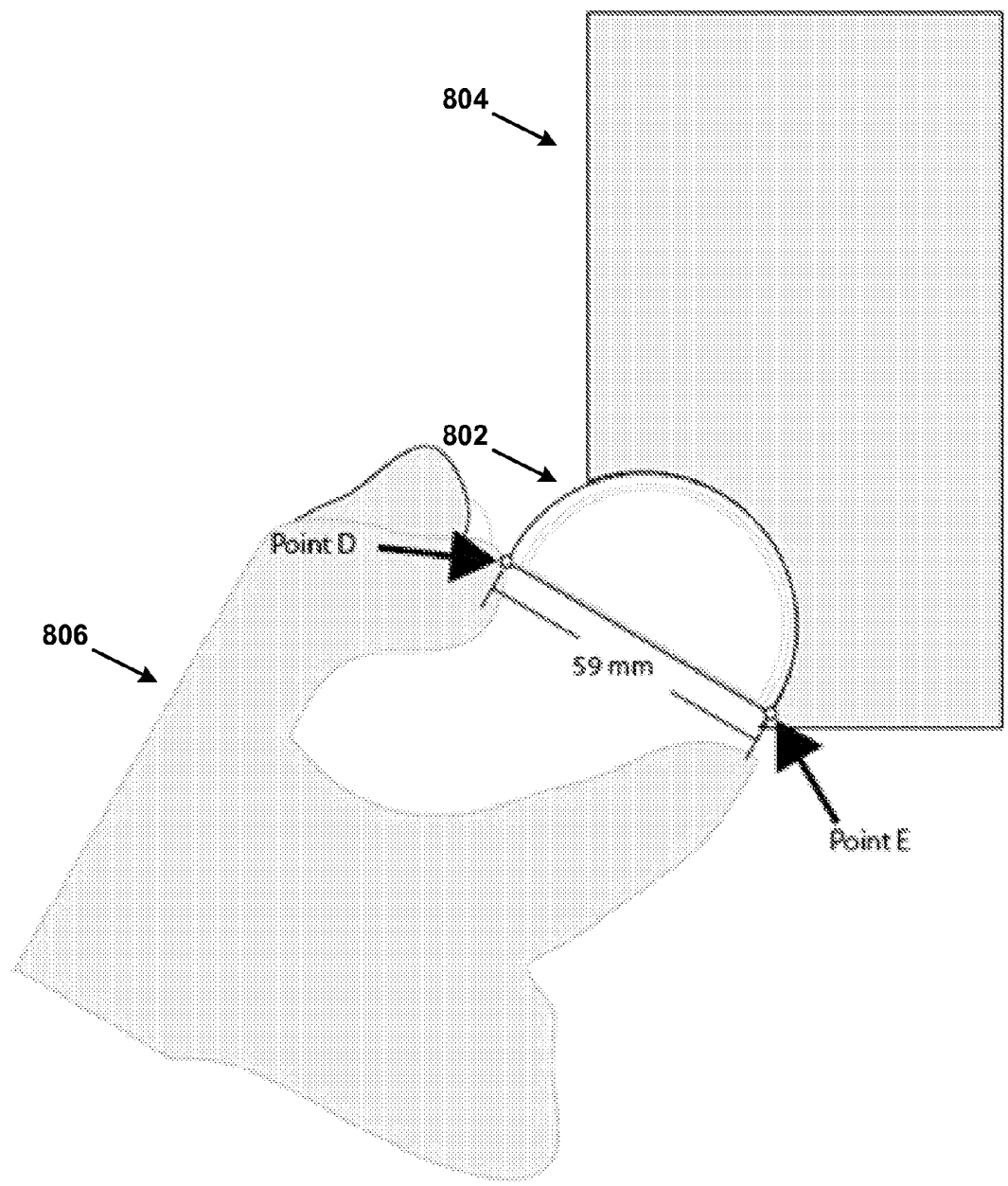

Regardless, FIG. 8E depicts a measurement of the positioned, rotated, and scaled template image 802. For instance, the computing device that displays the template image 802 and the target image 804 may determine that there are 59 millimeters (mm) between two points (point D and point E) of the template image 802.

It should be noted that any such measurement may not be to a physical or real-world scale. For example, the computing device may display the template image 802 and the target image 804 at a magnification of two or three times the actual sizes of the associated physical objects in order to make it easier for the user to bring about a precise fit of the template image 802 to the target image 804. However, other levels of magnification levels may be used instead. The measurement may involve determining the distance (e.g., the number of pixels) between pixels representing point D and pixels representing point E, or via some other technique.

Figure 8F:
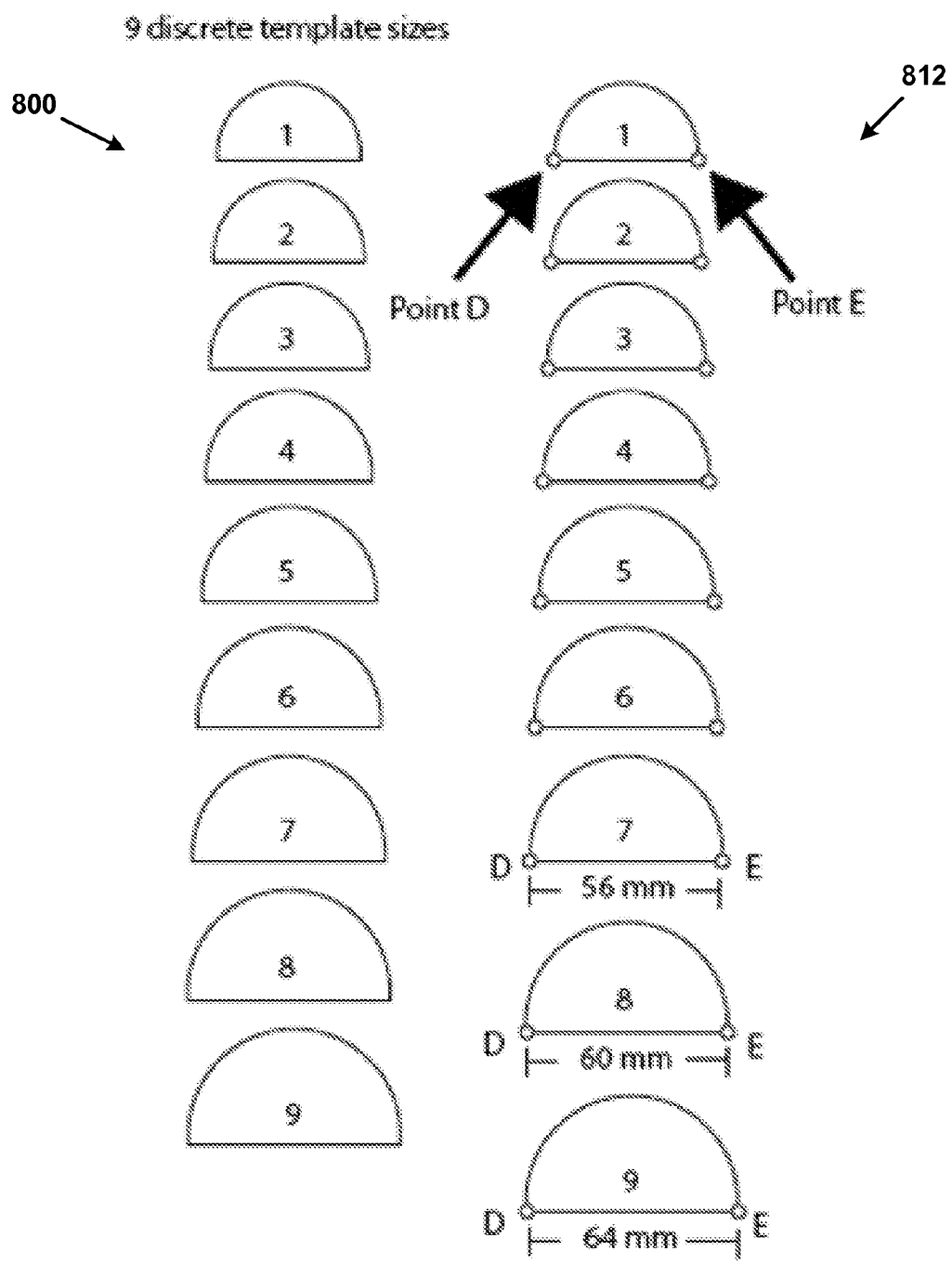

FIG. 8F depicts the 9 discrete template sizes 800, along with the 9 discrete template sizes marked with point D and point E 812 ("the marked 9 discrete template sizes 812"). For each of the marked 9 discrete template sizes 812, the respective point D and point E are marked accordingly. For the three largest of the marked 9 discrete template sizes 812, the distance between these points are given as 56 mm, 60 mm, and 64 mm, respectively. Since each vendor may produce joint replacement hardware in a limited number of sizes, such as the 9 discrete template sizes 800, it is desirable for the user-selected scale of the template image 802 to be mapped to one of these sizes.

Figure 8G:
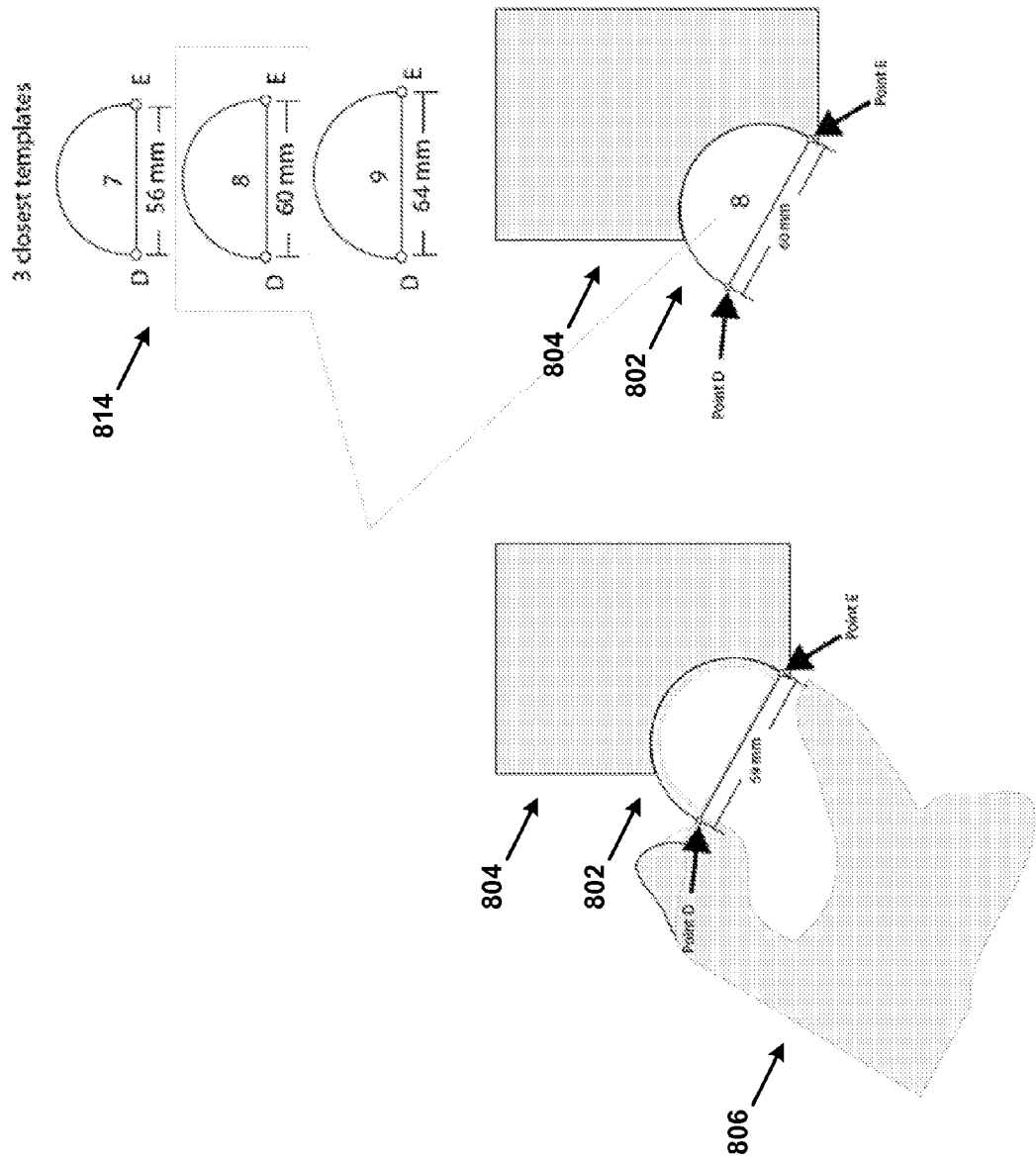

FIG. 8G depicts such a mapping. As shown in FIG. 8E, the distance between point D and point E of template image 802 is measured at 59 mm. Since there is no template of this size in the 9 discrete template sizes 800, the computing device may select (perhaps automatically) a template size from the 9 discrete template sizes 800 that has the closest size, i.e., the 60 mm template size. On the other hand, the computing device might display one or more of the n closest template sizes from the 9 discrete template sizes 800 and allow the user to select a template size. For instance, in FIG. 8G, the three closest templates 814 may be displayed, and the user may select one of them. The computing device may then replace the template image 802 with the selected template, and orient the selected template in the same or substantially the same position and rotation as the template image 802.

In an alternate embodiment, the computing device may display the scaling of template image 802 on a discrete, rather than a continuous, basis. For example, given the 9 discrete template sizes 800, as the user scales (increases or decreases) the size of template image 802, the computing device may only display the template image 802 at the closest size from the 9 discrete template sizes 800. Thus, the displayed size of template image 802 may "jump" between the 9 discrete template sizes 800 instead of taking on a multitude of sizes in between each of the 9 discrete template sizes 800.

The approach depicted in FIGS. 8A, 8B, 8C, 8D, 8E, 8F, and 8G may have several advantages over other ways of performing digital image templating. First, it is rapid and precise. Second, by allowing a user to substantially simultaneously position and rotate the template image, the traditional method of placing a clear sheet containing an outline in the shape of the template over a radiographic image is simulated. Thus, these embodiments may appeal to physicians due to their similarity with the traditional method.

Third, allowing the user to scale the template image is a significant improvement over manual templating. When templating is done manually, the user guesses the template size, selects a template of that size, and then positions and rotates that template over the radiographic image. If the selected template does not properly fit the radiographic image, the user must select a different template and then repeat the positioning and rotating steps. With the techniques described herein, the user need only select one template, and then position, rotate and scale this template image accordingly. Even with previous digital templating systems, the sizing steps would still need to be performed serially, resulting in a similarly lengthy process. Thus, the techniques herein serve to reduce the amount of time and labor a physician needs to invest in determining, for example, joint replacement hardware to use in a surgical procedure.

Fourth, the previous systems do not allow the user to simultaneously adjust the positioning, rotation, and/or scale of the actual template to the target image. The lack of such a feature is disadvantageous in general, as well as for more complex bone anatomy and/or more complex template shapes. These previous systems usually require complex image analysis or placement and measurement of a simple template image shape that does not represent the actual template. The result is that the user often has to still re-position and re-size the template image following automatic methods, because the simple shape does not approximate complex boney anatomy. The previous systems may also be unable to anticipate the correct placement of the image template, as each individual surgeon has their own preferences when placing templates.

These techniques may also benefit from one or more additional, optional features. For instance, the computing device may prevent the user from scaling the template image 802 to a size greater than the largest corresponding template size of the available template sizes (e.g., the 9 discrete template sizes 800). Likewise, the computing device may prevent the user from scaling the template image 802 to a size smaller than the smallest corresponding template size of the available template sizes. In this way, the user may be prevented from fitting a digital template of a size that is not available.

Another optional feature is to allow the computing device to display the template image 802 and the target image 804 in three dimensions (in 3D). This displaying may involve simulated 3D on a 2D screen, or actual 3D via, for instance, a holographic image. When such a feature is enabled, the user may be able to position, rotate, and scale the template image 802 in the three dimensions. The positioning could involve the user moving the template image 802 in a 3D space that is defined by an x-axis, y-axis, and a z-axis. The rotation could involve the user rotating the template image 802 around any one or more of these axes (e.g., to make use aeronautical terms, the user would be adjusting the pitch, roll, and/or yaw of the template image 802). The scaling could involve the user adjusting the magnification of the template image 802 in all three dimensions.

Figure 10:
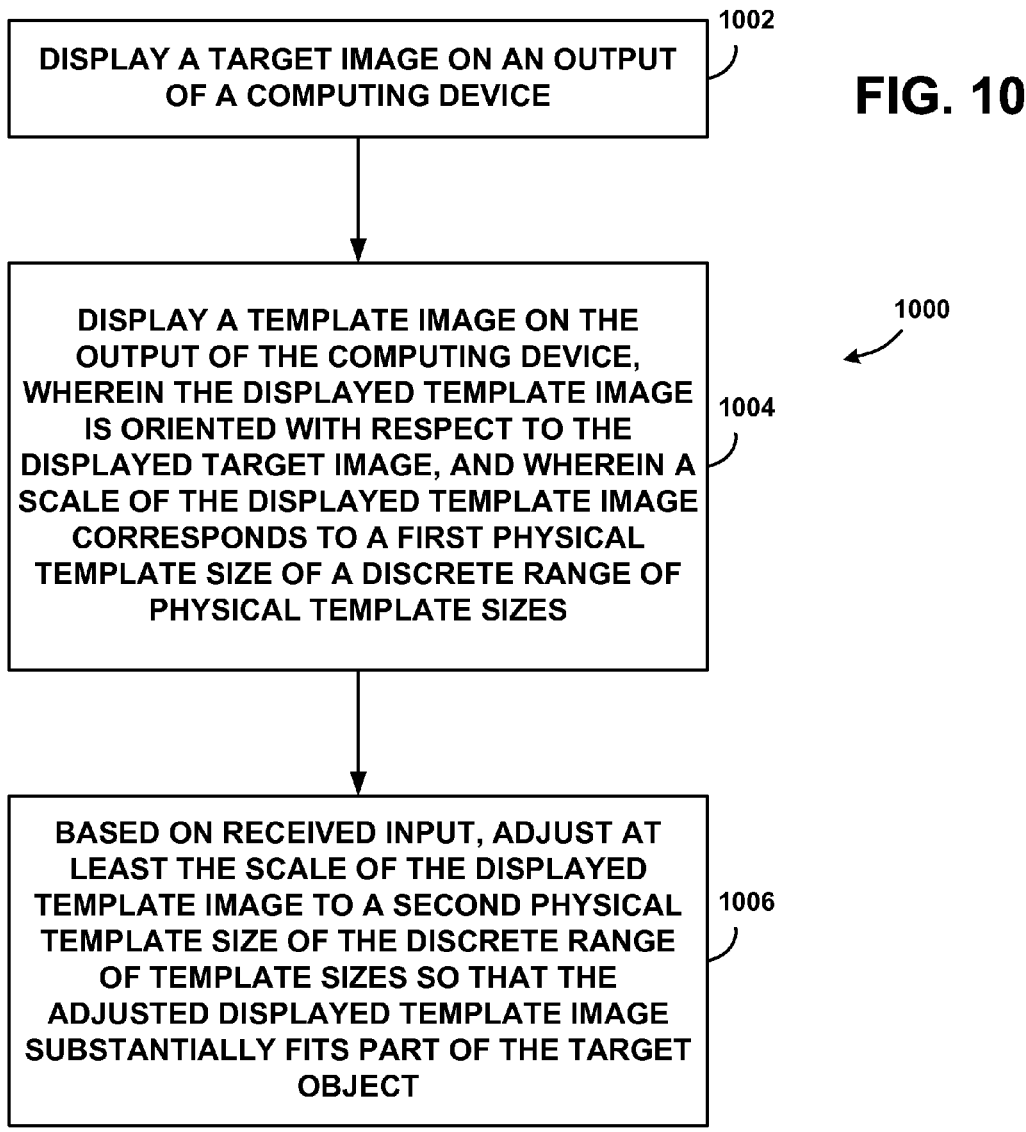
FIG. 10 is a fourth flow chart, in accordance with an example embodiment.

FIGS. 9 and 10 are flow charts 900 and 1000, respectively, of additional example embodiments for digital templating. It should be understood that, for each of these flow charts, more or fewer steps may be used. Thus, for example, steps may be added to or omitted from flow chart 900 or flow chart 1000. Further, the ordering of the steps in each flow chart is for purposes of example, and other orders of steps may be used. Additionally, flow charts 900 and 1000 may be combined with one another, or with flow chart 600 or flow chart 700, in whole or in part, without departing from the scope of the invention. Thus, as a whole, it should be understood that these flow charts are intended to be illustrative rather than limiting.

At step 902 of flow chart 900, a target image may be displayed on an output of a computing device. At step 904, a template image may also be displayed on the output of the computing device such that the displayed template image is oriented with respect to the displayed target image. At step 906, perhaps based on received input, at least a scale of the displayed template image may be adjusted so that the adjusted displayed template image substantially fits part of the displayed target image.

The displayed template image may also be oriented with respect to the displayed target image according to a rotation and a position. In this case, adjusting at least the scale of the displayed template image may involve also adjusting the rotation and/or position of the displayed template image so that the adjusted displayed template image substantially fits the part of the displayed target image. At least two of the scale, the rotation, and the position of the displayed template image are adjusted substantially simultaneously.

At step 908, a physical template size may be selected from a discrete range of physical template sizes. This selection may take place such that, out of the physical template sizes in the discrete range, a physical template of the selected physical template size is a closest match to the adjusted scale. Then, at step 910, a representation of the selected physical template size may be displayed on the output of the computing device. Displaying the representation of the selected physical template size may involve displaying a representation of the physical template of the selected physical template size.

Flow chart 1000 is arranged according to another example embodiment. At step 1002, a target image may be displayed on an output of a computing device. At step 1004, a template image may also be displayed on the output of the computing device such that the displayed template image is oriented with respect to the displayed target image, and a scale of the displayed template image corresponds to a first physical template size of a discrete range of physical template sizes.

At step 1006, perhaps based on received input, at least the scale of the displayed template image may be adjusted to a second physical template size of the discrete range of template sizes so that the adjusted displayed template image substantially fits part of the target image. The displayed template image may be oriented with respect to the displayed target image according to a rotation and a position. Adjusting at least the scale of the displayed template image may involve also adjusting the rotation and/or position of the displayed template image so that the adjusted displayed template image substantially fits the part of the displayed target object. Additionally, at least two of the scale, the rotation, and the position of the displayed template image may be adjusted substantially simultaneously.

For the methods of both flow charts 900 and 1000, the displayed target image may depict a radiographic image including a bone, and the displayed template image may depict a replacement part for the bone. Alternatively, the displayed template image may depict a fixation implant for the bone. Displaying the template image may include displaying the template image overlaying the target image such that at least one of the template image and the target image are displayed in a semi-transparent fashion. Additionally, the displayed target image may be three-dimensional, the displayed template image may be three-dimensional, and adjusting the scale of the displayed template image may occur in three dimensions.

Additionally, in the methods of both flow charts 900 and 1000, the template image may be displayed by a first application, and the target image may be displayed by a second application. The first and second applications may be independent of one another such that the first application does not have access to program instructions or memory used by the second application. Additionally, the first application may not be able to communicate with the second application.

V. Additional Features for Templating Applications

The templating application described by the embodiments herein has a valuable characteristic, in that physicians may spend a significant portion of their time using this software to perform their tasks. This virtual "face time" with busy physicians can be helpful for implant hardware vendors, as these vendors often find it difficult to schedule meetings with physicians. Thus, the templating application may include one or more windows, banners, or sections that are used for purposes not directly related to fitting templates to bone structures. In these windows, banners, or sections, the templating application may display information regarding just one vendor or multiple vendors.

For instance, before, during, or after a templating procedure, the templating application may display some form of advertisement to the user. This advertisement may be contextual, and therefore display information related to the templating procedure being performed. Thus, if the user is fitting a template of hip replacement implant hardware, the advertisement might display additional types of hip replacement implant hardware, new models of implant hardware, or upcoming training courses on hip replacement procedures. Thus, the advertisement may include images, text, or both, and any included images may be static or animated. Further, the images or text may incorporate hyperlinks to additional information, such as content found on one or more web logs (blogs), message boards or other types of online forums, social networking web sites, or other content.

It should be understood that blogs may be online diaries or reporting sites, on which one or more individuals may publish commentary, news, opinions, or other items of interest. Blog entries may be published regularly or irregularly, and may include text and other types of media. There are millions of blogs on the Internet. Additionally, message boards may include online discussion forums that typically involve multiple users posting articles or messages in discussion threads. These threads may be organized logically into specific or general topics or subjects. Like blog entries, message board posts may include text as well as other types of media. Further, social networking web sites may be online communities of individuals connected by common interests, background, or activities. These individuals may be able to create, share, and collaborate on various forms of content. Popular social networking web sites include WIKIPEDIA®, YOUTUBE®, TWITTER®, FACEBOOK®, FLICKR®, and MYSPACE®.

In an illustrative example, a physician may initiate the templating application. In response, the templating application may display an advertising window containing a graphical link to an implant hardware vendor's web site. As the physician chooses a template from a given vendor, the window may display the vendor's latest hardware offerings. During the templating procedure, the window may display dates and times of the vendor's upcoming training courses. After the templating is complete, the physician may be offered the opportunity to read blogs, forums, or social networking sites that feature content related to the type of procedure for which the physician performed the templating.

Advantageously, from what is offered in the advertising window, the physician may be able to obtain information that he or she would not have otherwise known existed. Compared to traditional print advertising, which is largely unread, advertising in the templating application can be focused on the particular interests of a specific user.

VI. Conclusion

Example embodiments have been described above. Those skilled in the art will understand, however, that changes and modifications may be made to these embodiments without departing from the true scope and spirit of the invention, which is defined by the claims. Functionally equivalent methods and apparatuses within the scope of the disclosure, in addition to those enumerated herein, will be apparent to those skilled in the art from the foregoing descriptions. Such modifications and variations are intended to fall within the scope of the appended claims. It is also to be understood that the terminology used herein is for the purpose of describing particular embodiments only, and is not intended to be limiting.

For instance, the term "physician" generally refers to any medical professional who may perform any templating function discussed herein. This individual need not be a licensed doctor. Further, the term "user" applies to any person or thing that may interact with the templating applications. Also, the term "bone structure" refers to one or more bones that may be coupled to one or more joints or other parts of a skeletal system.

It should be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present.

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Despite the focus of these example embodiments, the methods and devices disclosed herein are not limited to use in joint replacement procedures or orthopedics in general. In addition to the uses described above, the present invention can be used in fields such as architecture, space planning, and civil engineering, or any other field where a template is matched to features depicted in an image. Furthermore, the methods and devices disclosed herein may operate on or make use of a wide range of physical or logical computer hardware components, and may be implemented on any type of software platform.

What is claimed is:

1. A method comprising:
   displaying a target image of a subject on an output of a computing device;
   displaying a digital template image on the output of the computing device, wherein the displayed digital template image is an outline of a shape of an implantable member for implantation in the subject and is oriented with respect to the displayed target image;
   receiving one or more inputs to the computing device from a user simultaneously selecting at least two parts of the displayed digital template image;
   based on the received input of selecting at least two parts of the displayed digital template, adjusting the displayed digital template image, wherein adjusting the displayed digital template image alters at least one of a scale of the displayed digital template image, a rotation of the displayed digital template image, or a position of the displayed digital template image so that the adjusted displayed digital template image substantially fits a selected part of the displayed target image;
   selecting a physical template size from measuring the adjusted scaled displayed digital template from a discrete range of a plurality of physical template sizes, wherein, out of the physical template sizes in the discrete range, a physical template of the selected physical template size is a closest match to the adjusted scaled displayed digital template; and
   displaying the adjusted scaled displayed digital template image as a discrete physical size of the implantable member on the output of the computing device that is chosen from a discrete range of virtual sizes;
   wherein displaying the adjusted digital template image includes a change in size of the displayed digital template which jumps between at least a selected sub-plurality of a plurality of discrete digital template sizes from a range of discrete digital template sizes;
   wherein the changing in size is based on the received one or more inputs of at least scaling the displayed digital template image.

2. The method of claim 1, wherein the displayed digital template image is oriented with respect to the displayed target image according to the received input to adjust at least two of the scale of the displayed digital template image, the rotation of the displayed digital template image, and the position of the displayed digital template image so that the adjusted displayed digital template image substantially fits the selected part of the displayed target image.

3. The method of claim 2, wherein all of the scale, the rotation, and the position of the displayed digital template image are adjusted based on the received input;
   wherein at least two of the scale, the rotation, and the position of the displayed digital template image are adjusted simultaneously.

4. The method of claim 1, wherein the displayed target image depicts a radiographic image including a bone, and wherein the displayed digital template image of the member depicts at least one of a fixation implant for the bone or a replacement part for the bone.

5. The method of claim 1, wherein displaying the digital template image comprises:
   displaying the digital template image overlaying the target image, and wherein at least one of the digital template image and the target image are displayed in a semi-transparent fashion.

6. The method of claim 1, wherein the displayed target image is three-dimensional, the displayed digital template image is three-dimensional, and adjusting the scale of the displayed digital template image occurs in three dimensions.

7. A method comprising:
   displaying a target image on an output of a computing device;
   displaying a digital template image on the output of the computing device with a touch screen, wherein the displayed digital template image including an outline in a shape of a member to be implanted that is oriented with respect to the displayed target image, and wherein a scale of the displayed digital template image corresponds to a first physical template size of a discrete range of a plurality of physical template sizes;
   touching a touch screen at a first point and a second point relative to the displayed digital template image to adjust at least two of the scale, the rotation, and the position of the displayed template image relative to the target image;

based on received input from touching the screen, adjusting at least the scale of the displayed digital template image to a second physical template size that is selected from the discrete range of the plurality of template sizes, wherein the discrete range of the plurality of physical template sizes includes only discrete physical template sizes including the first physical template size and the second physical template size; and after adjusting the scale, displaying the adjusted digital template image over the target image that is at the second physical template size substantially fits part of the target image;

wherein displaying the adjusted digital template image includes a change in size of the displayed digital template which jumps between at least a selected sub-plurality of a plurality of discrete digital template sizes from a range of discrete digital template sizes;

wherein the changing in size is based on the received input of at least scaling the displayed digital template image.

8. The method of claim 7, wherein the displayed digital template image is oriented with respect to the displayed target image according to a rotation and a position, and wherein adjusting at least the scale of the displayed digital template image comprises:

also adjusting the rotation and position of the displayed digital template image so that the adjusted displayed digital template image substantially fits the part of the displayed target object;

wherein all of adjusting the rotation, position, and scale occur simultaneously by touching the touch screen.

9. The method of claim 8, wherein at least two of the scale, the rotation, and the position of the displayed digital template image are adjusted simultaneously.

10. The method of claim 7, wherein the displayed target image is three-dimensional, the displayed digital template image is three-dimensional, and adjusting the scale of the displayed digital template image occurs in three dimensions.

11. The method of claim 3, wherein the displayed digital template image is oriented with respect to the displayed target image according to a rotation and a position substantially automatically by a computing device.

12. The method of claim 11, wherein the target image is a screen shot of an image of the subject from a first application executable by a first computer system;

wherein displaying the digital template image, adjusting at least a scale of the displayed digital template image, and selecting a physical template size from a discrete range of physical template sizes is a second application separate from and does not communicate with the first application.

13. The method of claim 8, wherein adjusting the rotation and position of the displayed digital template image is further performed automatically with a computer system.

14. The method of claim 3, wherein displaying the digital template image on the output of the computing device includes displaying the digital template image on a touchscreen interface;

wherein receiving the input to the computing device from the user selecting at least two parts of the displayed digital template image includes the user contacting the touchscreen interface at a first point and a second point to adjust at least two of the scale, the rotation, and the position of the displayed template.

15. The method of claim 14, wherein the displayed digital template image is adjusted simultaneously via the touchscreen interface for at least two of the scale, the rotation, and the position of the displayed digital template image.

16. The method of claim 3, wherein displaying the target image of the subject on the output of the computing device includes communicating with a server via the internet to retrieve the target image.

17. A method comprising:

selecting a target image of a subject for display on a touchscreen display of a computing device;

viewing a displayed digital template image that is displayed on the touchscreen display of the computing device, wherein the displayed digital template image is an outline of a shape of an implantable member for implantation in the subject and is oriented with respect to the displayed target image;

touching the touchscreen display at a first point with a first finger and at a second point with a second singer to touch two points simultaneously on the touchscreen to select at least two parts of the displayed digital template image to provide input to the computing device;

while touching the touchscreen with the first finger and the second finger, moving at least the first finger or the second finger to adjust the displayed digital template image, wherein adjusting the displayed digital template image alters at least one of a scale of the displayed digital template image, a rotation of the displayed digital template image, or a position of the displayed digital template image so that the adjusted displayed digital template image substantially fits a selected part of the displayed target image; and viewing the touchscreen display to view the adjusted displayed digital template image as a single discrete size of the digital template object that is selected from one of a plurality of discrete digital template image sizes;

wherein viewing the touchscreen to view the adjusted displayed digital template image includes viewing a change of size that includes a jump of the displayed digital template object between at least a first discrete digital template image size and a second discrete template image size of the plurality of discrete digital template image sizes;

wherein the viewing the change of size is based on one or more inputs of at least scaling the displayed digital template image.

18. The method of claim 17, further comprising: selecting a physical template size from measuring the adjusted displayed digital template scale from a discrete range of a plurality of physical template sizes, wherein, out of the physical template sizes in the discrete range, a physical template of the selected physical template size is a closest match to the adjusted scale.

19. The method of claim 18, wherein only the determined representation of the selected physical template size is illustrated on the touch screen.

20. The method of claim 17, further comprising:

operating a camera to acquire the target image for display on the touch screen.

21. The method of claim 17, wherein selecting the target image occurs via an internet connection to a server.

22. The method of claim 18, wherein the plurality of discrete digital template image sizes includes nine (9) discrete and separate digital template images for viewing.

23. The method of claim 17, further comprising:

collaborating via the computing device regarding the displayed digital template image.

* * * * *

UNITED STATES PATENT AND TRADEMARK OFFICE
CERTIFICATE OF CORRECTION

PATENT NO. : 8,917,290 B2  
APPLICATION NO. : 13/018021  
DATED : December 23, 2014  
INVENTOR(S) : Paul Richard Beck Page 1 of 1

It is certified that error appears in the above-identified patent and that said Letters Patent is hereby corrected as shown below:

In the specification,

Column 6, Line 1, Delete "table" and insert --tablet--, therefor.

Column 6, Line 7, Delete "communication system 110" and insert --computing system 100--, therefor.

In the claims,

Column 26, Claim 17, Line 17, Delete "singer" and insert --finger--, therefor.

Signed and Sealed this
Twelfth Day of May, 2015

Michelle K. Lee
*Director of the United States Patent and Trademark Office*